(12) United States Patent
Rong et al.

(10) Patent No.: US 11,434,466 B2
(45) Date of Patent: *Sep. 6, 2022

(54) PROCESS OF CULTIVATING MICROALGAE AND A JOINT METHOD OF SAME WITH A DENITRATION PROCESS

(71) Applicants: CHINA PETROLEUM & CHEMICAL CORPORATION, Beijing (CN); RESEARCH INSTITUTE OF PETROLEUM PROCESSING, SINOPEC, Beijing (CN)

(72) Inventors: Junfeng Rong, Beijing (CN); Xuhua Zhou, Beijing (CN); Lin Cheng, Beijing (CN); Junying Zhu, Beijing (CN); Xugeng Huang, Beijing (CN); Baoning Zong, Beijing (CN)

(73) Assignees: CHINA PETROLEUM & CHEMICAL CORPORATION, Beijing (CN); RESEARCH INSTITUTE OF PETROLEUM PROCESSING, SINOPEC, Beijing (CN)

(\*) Notice: Subject to any disclaimer, the term of this patent is extended or adjusted under 35 U.S.C. 154(b) by 230 days.

This patent is subject to a terminal disclaimer.

(21) Appl. No.: 15/328,339

(22) PCT Filed: Mar. 17, 2015

(86) PCT No.: PCT/CN2015/000180
§ 371 (c)(1),
(2) Date: Jan. 23, 2017

(87) PCT Pub. No.: WO2016/011784
PCT Pub. Date: Jan. 28, 2016

(65) Prior Publication Data
US 2017/0211036 A1 Jul. 27, 2017

(30) Foreign Application Priority Data

Jul. 23, 2014 (CN) .......................... 201410352725.7
Oct. 21, 2014 (CN) .......................... 201410563214.X

(51) Int. Cl.
*B01D 53/56* (2006.01)
*C12N 1/12* (2006.01)
(Continued)

(52) U.S. Cl.
CPC ............... *C12N 1/12* (2013.01); *B01D 53/56* (2013.01); *B01D 53/78* (2013.01); *B01D 53/84* (2013.01);
(Continued)

(58) Field of Classification Search
CPC .... C12N 1/12; C12N 1/125; B01D 2251/106; B01D 2251/504; B01D 53/56;
(Continued)

(56) References Cited

U.S. PATENT DOCUMENTS

| 4,383,038 A | 5/1983 | Leavitt |
| 8,262,776 B2 * | 9/2012 | Hazlebeck ............. C12M 21/02 |
| | | 435/266 |
| 2011/0126513 A1 | 6/2011 | Lee et al. |

FOREIGN PATENT DOCUMENTS

| CN | 1923341 A | 3/2007 |
| CN | 101082024 A | 12/2007 |

(Continued)

OTHER PUBLICATIONS

Lakaniemi et al., Microbial Biotechnology (2012) 5(1), 69-78.*
(Continued)

*Primary Examiner* — David W Berke-Schlessel
*Assistant Examiner* — Trent R Clarke
(74) *Attorney, Agent, or Firm* — Novick, Kim & Lee, PLLC; Allen Xue

(57) ABSTRACT

The present invention provides a process of cultivating microalgae and a joint method of same jointed with deni-
(Continued)

tration. During the microalgae cultivation, EM bacteria is added into the microalgae suspension. In the nutrient stream for cultivating microalgae, at least one of the nitrogen source, phosphorus source and carbon source is provided in the form of a nutrient salt. During the cultivation, the pH of the microalgae suspension is adjusted with nitric acid and/or nitrous acid. The joint method includes (1) a step of cultivating microalgae; (2) a separation step of separating a microalgae suspension obtained from step (1) into a wet microalgae (microalgae biomass) and a residual cultivation solution; and (3) a NOx absorbing/immobilizing step of denitrating an industrial waste gas with the residual cultivation solution obtained from step (2). The nutrient stream absorbed with NOx obtained from step (3) is used to provide nitrogen source to the microalgae cultivation of step (1).

13 Claims, 8 Drawing Sheets

(51) Int. Cl.
  *B01D 53/78* (2006.01)
  *B01D 53/84* (2006.01)
  *C12R 1/89* (2006.01)
(52) U.S. Cl.
  CPC .. *B01D 2251/106* (2013.01); *B01D 2251/504* (2013.01); *B01D 2251/95* (2013.01); *B01D 2256/22* (2013.01); *B01D 2259/802* (2013.01); *C12N 1/125* (2021.05); *C12R 2001/89* (2021.05); *Y02A 50/20* (2018.01)
(58) Field of Classification Search
  CPC .... B01D 53/78; B01D 53/84; B01D 2251/95; B01D 2259/802; C12R 2001/89
  See application file for complete search history.

(56) References Cited

FOREIGN PATENT DOCUMENTS

| | | |
|---|---|---|
| CN | 101363005 A | 2/2009 |
| CN | 102061261 A | 5/2011 |
| CN | 103103126 A | 5/2013 |
| CN | 103103130 A | 5/2013 |
| CN | 103805514 A | 5/2014 |
| CN | 103933848 A | 7/2014 |
| DE | 19607389 A1 | 9/1997 |
| GB | 2492239 A | 12/2012 |
| JP | S31-6089 A | 7/1931 |
| JP | 53-096381 A | 8/1978 |
| JP | H08257356 A | 10/1996 |
| KR | 20120098256 A | 9/2012 |
| WO | 9822201 A1 | 5/1998 |
| WO | 2008145719 A1 | 12/2008 |

OTHER PUBLICATIONS

Borde et al., Bioresource Technology 86 (2003) 293-300.*
Sorokin et al., 1958. Plant Physiol. 33, 109-113.*
Zhou et al., CN 101082024, machine translation.*
Kliphuis, A.M.J., PhD Thesis, Wageningen University, Wageningen, NL( 2010).*
Zakaria, Z., Gairola, S. and Sharill, N. M., Effective Microorganisms (EM) Technology for Water Quality Restoration and Potential for Sustainable Water Resources and Management, 2010, International Congress on Environmental Modelling and Software, vol. 142, pp. 1-9 (Year: 2010).*
NPL document "Microzyme liquid" is the webpage at http://uniservicebaltica.eu/offer/products/biological-environmental-products/microzyme-liquid/accessed Jun. 8, 2019, published online Feb. 1, 2001 according to Google (see p. 1) (Year: 2001).*
Fathurrahman Lananan et al., Symbiotic bioremediation of aquaculture wastewater in reducing ammonia and phosphorus utilizing Effective Microorganism (EM-1) and microalgae (*Chlorella* sp.), 2014, International Biodeterioration & Biodegradation, vol. 95, 127-134, published online Jul. 17, 2014. (Year: 2014).*
Google machine translation of CN103805514, Wang et al. (Year: 2014).*
European Patent Office machine translation of WO 97/31700, Koppe et al. (Year: 1997).*
Donna C. Sullivan and Stanley W. Chapman, Bacteria That Masquerade as Fungi, 2010, Proc. Am. Thorac. Soc., vol. 7, pp. 216-221. (Year: 2010).*
Teruo Higa and James F. Parr, Beneficial and Effective Microorganisms for a Sustainable Agriculture and Environment, 1994, International Nature Farming Research Center, Atami, Japan, pp. 1-16. (Year: 1994).*
Qingming Hu, "Cultivating microalgae by Exhaust gas achieves success in Shijiazhuang", Refinery Energy Conservation in Petroleum & Petrochemical Industry., Aug. 31, 2013, No. 08, ISSN: 2095-1493.
European Patent Office, Extended European Search Report for EP application No. 15824219, dated May 18, 2018.
The State Intellectual Property Office of People's Republic of China, First Office Action of CN 201310424935.8 (corresponding Chinese patent application), dated Aug. 3, 2016.
The State Intellectual Property Office of People's Republic of China, Second Office Action of CN 201310424935.8 (corresponding Chinese patent application), dated Mar. 31, 2017.
Yongxu Cheng, Culture of living foods, Aug. 2005, China Agriculture Publishing House, ISBN 9787109098121, pp. 50-100.

* cited by examiner

PROCESS OF CULTIVATING MICROALGAE AND A JOINT METHOD OF SAME WITH A DENITRATION PROCESS

TECHNICAL FIELD

The present invention relates to a process of cultivating microalgae and a joint method of same with denitration of an industrial waste gas.

BACKGROUND

Energy source and environment are important challenges encountered by human being for sustainable development. On the one hand, fossil energy sources are non-renewable, and it is emergent to develop alternative energy sources. On the other hand, the waste gas and sewage generated from the consumption of fossil energy sources have been resulting in severe impact on the environment, which need to be solved synthetically.

Microalgae is a widely distributed lower plant comprising a great deal of categories, which converts the optical energy into a chemical energy of carbohydrates, such as fat or starch, by effective photosynthesis, and thus is called as a "sun driven activating factory". The generation of biological energy and chemicals by microalgae is hopeful to achieve the dual purposes of substituting the fossil energy sources and cleaning the waste gas and sewage.

In the nature, there is a complicated ecological relationship between microalgae and bacteria. Some specific microalgae and bacteria may benefit one another, while some others may inhibit one another. A known difficulty of cultivating microalgae is the presence of abundant harmful bacteria in water and air, which is unfavorable for the growth of microalgae, even resulting in a failed cultivation. When an open system is used to cultivate microalgae, it is impossible to achieve an aseptic state, then it is under high risk of bacteria contamination. A closed cultivation system with rigorous sterilization can achieve an aseptic state, while for a large scale of microalgae cultivation, it is too expensive.

NOx in an industrial waste gas is one of the significant air pollutants. NOx not only creates photochemical fog and acid rain, but also results in severe greenhouse effect. NOx is also one of the principle inducements of atmospheric haze. The denitration of an industrial waste gas is thus more and more regarded. The processes of denitrating an industrial waste gas can be classified into a dry process and a wet process. Selective Catalytic Reduction (SCR) and Selective non-Catalytic Reduction (SNCR) are conventional dry processes, which both involve high costs of investment and operation, where NOx is reduced to low valuable nitrogen gas without resourcing NOx. The wet process absorbs NOx in a waste gas and immobilizes it in an absorption solution. Such a process has low costs of investment and operation, whilst two problems need to be solved. Firstly, NOx in the industrial waste gas is mainly in the form of NO (generally 90% or more), which is little soluble in water, such that a corresponding means is needed to solve the problem involving the solubility of NO. Secondly, nitrous acid or nitrite is generally unavoidable during the absorption, which is hypertoxicity, such that a corresponding means is needed to the problem involving the separation, re-use or disposal thereof.

On the other hand, nitrogen is one of the nutritive elements consumed most rapidly and most readily lacking during the growth of microalgae. The consumption of a great amount of nitrogenous fertilizer is costly for microalgae cultivation. Therefore, it is desirable to combine the cultivation of microalgae and the denitration of an industrial waste gas, which on one hand can use NOx to provide nitrogenous fertilizer to the microalgae growth, so as to decrease the cost of microalgae cultivation; while on the other hand can purify the waste gas to reduce the discharge of NOx, benefiting the environment. There are some published documents disclosing processes of feeding an industrial waste gas into a cultivating device of microalgae for denitration; however, these processes involve some insoluble problems: (1) the denitration of an industrial waste gas using microalgae must solve the problems restricting the commercialization thereof, such as the illumination and mild climate conditions for cultivating microalgae, while the weather change necessarily resulting in varied efficiencies of denitration, such that the direct feeding of an industrial waste gas is difficult to match the emission operation of the industrial waste gas with the cultivation operation of microalgae, where the two operations interact therebetween to be insufficient to satisfy the requirement of reducing the emission from an industrial production; (2) nitrogen oxide (NO) is the main component of NOx, while NO is little soluble in water, such that the direct feeding of industrial waste gas cannot solve the problem of the great amount of water-insoluble NO in NOx to be little absorbed.

Abundant of NOx is produced from chemical industry. If microalgae is desired to immobilize NOx in the industrial waste gas, the immobilizing rate of NOx by microalgae should match the emitting rate of NOx from the industrial discharge, and the floor space occupied by the microalgae culturing device should be minimized. Generally, the biomass productivity of photoautotrophic microalgae isphotoautotrophic cultivation less than 30 $g \cdot m^{-2} \cdot d^{-1}$, which is reduced to less than 10 $g \cdot m^{-2} \cdot d^{-1}$ for an outdoor large-scale cultivation. With such a biomass productivity, the plant for denitration of an industrial waste gas will occupy a large area. Thus it is necessary to increase the biomass productivity of microalgae. A heterotrophic or mixotrophic cultivation by adding an organic carbon source is a feasible method of accelerating the growth of microalgae; however, after adding the organic carbon source, the microalgae suspension is quite readily to be polluted by harmful bacteria, resulting in rapid growth of the bacterial significantly faster than that of the microalgae, which even causes a failed microalgae cultivation.

A scaled microalgae cultivation needs abundant water. If water is not recycled, the cultivation is costly. Most of the known categories of microalgae cannot adapt to a high concentration ammonium solution, e.g., ammonium sulphate which is generally used as an inhibitor of microalgae. Meanwhile, when a nitrate is used to provide a nitrogen source to the microalgae, it is difficult to recycle water used in the cultivation, because metal ions accumulates in the cultivating water, resulting in an increased salinity, while a high salinity generally inhibits the growth of microalgae.

SUMMARY OF THE INVENTION

The first purpose of the present invention is to increase the biomass productivity of microalgae, in particular to increase the biomass productivity of heterotrophic cultivation and mixotrophic cultivation. The second purpose of the present invention is to avoid an aseptic operation during heterotrophic cultivation and mixotrophic cultivation. The third purpose of the present invention is to combine synthetically the cultivation of microalgae and the denitration of an industrial waste gas, which can not only use NOx as a nitrogen source for the growth of microalgae, but also avoid any interference caused by the different operation conditions between the waste gas emission and the microalgae cultivation. The fourth purpose of the present invention is to use an aqueous solution of nitric acid/hydrogen peroxide as an absorption solution for the denitration of an industrial waste gas, so as to avoid generation of any toxic nitrous acid, and to increase the availability of the hydrogen peroxide during the process.

Specifically, the present invention comprises, for example, the following aspects of contents.

In an aspect, the present invention provides a high efficiency process of cultivating microalgae, characterized in that during the cultivation, EM bacteria is added into the microalgae suspension.

In another aspect, the present invention provides a process of cultivating microalgae, wherein in the nutrient stream for cultivating microalgae, at least one of the nitrogen source, phosphorus source and carbon source is provided in the form of a nutrient salt, characterized in that during the cultivation, the pH of the microalgae suspension is adjusted with nitric acid and/or nitrous acid.

In another aspect, the present invention provides a joint method of cultivating microalgae and denitrating an industrial waste gas, comprising the steps of:
(1) a cultivation step of cultivating microalgae;
(2) a separation step of separating a microalgae suspension obtained from step (1) into a wet microalgae (microalgae biomass) and a residual cultivation solution;
(3) a NOx immobilizing step of denitrating an industrial waste gas with the residual cultivation solution obtained from step (2); and
(4) optionally, a drying step of drying the microalgae biomass obtained from step (2) to provide a microalgae product;
wherein a NOx immobilized nutrient stream obtained from step (3) is used to provide nitrogen source to the microalgae cultivation of step (1).

The step (3) above can be conducted by various ways.

In one preferable embodiment, the joint method involves an acid procedure, wherein the step (3) comprises:
(i) a sub-step of converting NOx in the industrial waste gas into nitric acid and/or nitrous acid; and
(ii) mixing the residual cultivation solution obtained from step (2) with the nitric acid and/or nitrous acid (preferably the nitric acid and optionally the nitrous acid) obtained from step (i), so as to achieve the denitration of an industrial waste gas.

In the embodiment, the solution obtained from the mixing is used as the NOx immobilized nutrient stream to provide nitrogen source to the microalgae cultivation in step (1).

In another preferable embodiment, the joint method involves an alkali procedure, wherein the step (3) comprises:
(i') immobilizing NOx in the industrial waste gas directly with the residual cultivation solution obtained from step (2).

In the embodiment, the NOx immobilized nutrient stream obtained from the step (i') is used to provide nitrogen source to the microalgae cultivation in step (i).

In another aspect, the present invention provides a system useful for the joint method of cultivating microalgae and denitrating an industrial waste gas, comprising, optionally from upstream to downstream:
a NOx immobilizing unit, useful for carrying out the denitration and providing a NOx immobilized nutrient stream;
a microalgae cultivating device, useful for cultivating the microalgae with the NOx immobilized nutrient stream;
a separator, useful for separating a microalgae suspension obtained from the microalgae cultivating device into a microalgae biomass and a residual cultivation solution; and
a recycle line, useful for recycling the residual cultivation solution obtained from the separator to upstream of the process, so as to immobilize the NOx in the industrial waste gas;
and optionally, a dryer, useful for drying the microalgae biomass to provide a microalgae product.

In one preferable embodiment, the NOx immobilizing unit has an inlet for the NOx-containing industrial waste gas, an inlet for the residual cultivation solution, an outlet for the NOx immobilized nutrient stream and an outlet for the purified industrial waste gas, and optionally an inlet for the nutrient solution.

In one preferable embodiment, the microalgae cultivating device has an inlet for the NOx-immobilized nutrient stream, an inlet for a microalgae strain, an outlet for the microalgae suspension, and optionally an inlet for the nutrient solution and optionally an inlet for the EM bacteria.

In one preferable embodiment, the separator has an inlet for the microalgae suspension, an outlet for the microalgae biomass and an outlet for the residual cultivation solution.

In one preferable embodiment, the recycle line links the outlet for the residual cultivation solution of the separator to the inlet for the residual cultivation solution of NOx immobilizing unit.

Preferably, in the method involving the acid procedure, the NOx immobilizing unit or the microalgae cultivating device has an inlet for the nutrient solution.

Preferably, in the method involving the alkali procedure, the microalgae cultivating device has an inlet for the nutrient solution.

In one preferable embodiment, the joint method involves the acid procedure, wherein the NOx immobilizing unit comprises a denitration reactor and a NOx immobilizing nutrient stream formulating device. In one preferable embodiment, the joint method involves the alkali procedure, wherein the NOx immobilizing unit is a denitration reactor. In one preferable embodiment, in the nutrient stream for cultivating microalgae, at least one of the nitrogen source, the phosphorus source and the carbon source is provided in the form of a nutrient salt of an alkali metal. In one preferable embodiment, during the cultivation, nitric acid and/or nitrous acid is used to adjust the pH of the microalgae suspension. In one preferable embodiment, in the nutrient stream for cultivating microalgae, the nitrogen source is provided in the form of an alkali nitrate and/or an alkali nitrite. In one preferable embodiment, the microalgae is cultivated by heterotrophic or mixotrophic cultivation. Further, in one preferable embodiment, when a microalgae is cultivated by the heterotrophic or mixotrophic cultivation, the organic carbon source used is at least one selected from the group consisting of sugar, organic acid, salt of an organic acid, alcohol, cellulose hydrolyzate and glucidtemns; preferably at least one of glucose, fructose, acetic acid, sodium acetate, lactic acid, ethanol, methanol and cellulose hydrolyzate, more preferably glucose. Further, in one preferable embodiment, when a microalgae is cultivated by the heterotrophic or mixotrophic cultivation, the organic carbon source used is controlled to have a concentration of 1 g/L microalgae suspension-30 g/L microalgae suspension, preferably 2 g/L microalgae suspension-10 g/L microalgae suspension. In one preferable embodiment, the cultivation is a photoautotrophic cultivation or a mixotrophic cultivation, with an illumination intensity of 1000-200000 lux. In one preferable embodiment, the process of cultivating microalgae according to the present invention further comprises separating a microalgae biomass from the microalgae suspension harvested, and recycling a residual cultivation solution obtained through the separation of the microalgae biomass to the microalgae cultivation. In particular, the prior art deems that nitrate is capable of being used as the nitrogen source for the microalgae cultivation. However, under certain situations, the accumulation of metal ions contained in the nitrate may probably inhibit the growth of microalgae. In accordance with the present invention, when an acid procedure is used, the addition of any extra nitrate is not needed, such that no more metal cations are additionally introduced, so as not to result in the accumulation of metal cations during the process. In one preferable embodiment, during the microalgae cultivation, EM bacteria is added into the microalgae suspension. The EM bacteria is added in an amount of $1 \times 10^5$ cells/L microalgae suspension-$9 \times 10^8$ cells/L microalgae suspension, preferably is $1 \times 10^6$ cells/L microalgae suspension-$5 \times 10^8$ cells/L microalgae suspension, further preferably is $1 \times 10^6$ cells/L microalgae suspension-$1 \times 10^8$ cells/L microalgae. In one preferable embodiment, in step (i) of the joint method, a wet denitration is used to convert NOx in the industrial waste gas into nitric acid. In one preferable embodiment, the absorption solution used to absorb NOx in the wet denitration consists of 0.5 m %-58 m % of nitric acid, 0.001 m %-25 m % of hydrogen peroxide and balance of water. In one preferable embodiment, the absorption solution used in the wet denitration consists of 10 m %-25 m % of nitric acid, 0.1 m %-1 m % of hydrogen peroxide and balance of water. The present invention achieves the following technical effects. According to the present invention, during the microalgae cultivation, nitric acid and/or nitrous acid is used to adjust the pH of the microalgae suspension, increasing greatly the microalgae cultivating efficiency. According to the present invention, the cultivation of microalgae and the denitration of an industrial waste gas are two relatively independent processes, avoiding the interference caused by the different operation conditions between the waste gas emission and the microalgae cultivation, and avoiding the difficult immobilization as abundant of NO insoluble in water. So, NOx in the industrial waste gas can provide nitrogen source to the microalgae without extra need of additional alkaline solution, which brings lower cost to the cultivating process according to the present invention. The present invention avoids the problem caused by accumulation of metal ions, allowing the cyclic utilization of the cultivating water system. According to the present invention, EM bacteria is added into the microalgae suspension, which can inhibit effectively the propagation of harmful bacteria, increasing significantly the growth rate of microalgae. The advantage of the present invention avoids the need of sterilization for a heterotrophic cultivation or a mixotrophic cultivation. According to the present invention, hydrogen peroxide with a low concentration and an aqueous nitric acid solution with a low concentration are used as an absorption solution for the denitration of an industrial waste gas, where a lower decomposition rate and a highly effective availability of hydrogen peroxide are achieved. According to the present invention, a dilute nitric acid is produced simultaneously with the denitration of an industrial waste gas, which dilute nitric acid is free of toxic nitrous acid and is more preferred to be used as the nitrogen source of microalgae cultivation.

Figure 1:
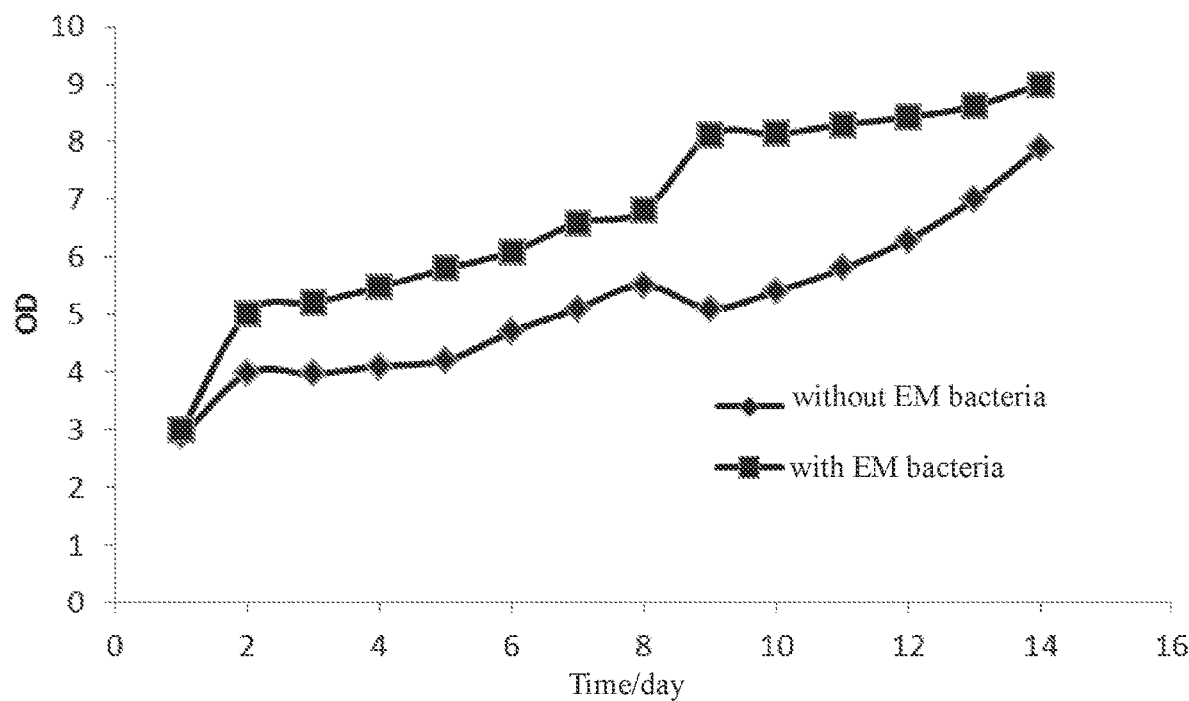
FIG. 1 represents a curve showing the growth of microalgae by photoautotrophic cultivation.

1: NOx immobilizing unit;
1-1: denitration reactor;
1-2: NOx immobilizing nutrient stream formulating device
2: microalgae cultivating device;
3: separator;
4: dryer;
5: $CO_2$ absorbing nutrient stream formulating device;
6: $CO_2$ microalgae cultivating device;
7: $CO_2$ microalgae cultivation separator
A: NOx-containing gas;
B: NOx immobilized nutrient stream;
C: purified gas;
D: microalgae strain;
E: nutrient solution;
F: residual cultivation solution;
G: wet microalgae;
H: microalgae product;
I: $CO_2$ absorbing microalgae nutrient solution;
J: $CO_2$ absorbing nutrient stream;
K: $CO_2$ absorbing microalgae strain;
L: $CO_2$; and
M: $CO_2$ cultivation microalgae suspension.

EMBODIMENTS

The embodiments of the present invention will be illustrated below, whilst it should be understood that the protection scopes of the present invention are not restricted thereto; instead, the protection scopes are defined by the claims attached. Unless otherwise defined, the scientific and technical terms used in the specification have the meanings conventionally known by those skilled in the art. For conflicting meanings of the terms, they shall subject to the definitions by the present specification. In accordance with the present invention, for example, medium/culture medium means an aqueous system used for the growth of microalgae therein during a microalgae cultivation, which comprises essential nutrient substances for the growth of microalgae, unless specifically designated. In accordance with the present invention, for example, nutrient stream means a stream comprising one or more nutrient sources, such as a nitrogen source, a phosphorus source or a carbon source, used to formulate the medium, unless specifically designated. In accordance with the present invention, for example, microalgae suspension means a system formed by adding a microalgae into a culture medium, unless specifically designated. In accordance with the present invention, when a technical solution is defined in an open mode, e.g., by "comprising", "containing", or the like, to provide some members, those skilled in the art would understand that an embodiment consisting of, or consisting essentially of, these members can be used to practice the technical solution obviously. Therefore, those skilled in the art would understand that a technical solution defined in an open mode also encompasses the specific embodiments defined with "consisting of", or with "consisting essentially of". In the context of the specification, any features or technical means not discussed specifically will be understood with the meanings known in the art without any substantive modification, unless otherwise designated. Moreover, any embodiment described in the specification can be associated freely with one or more other embodiments described in the specification, and the technical solution or idea formed therefrom is deemed as a part of the original disclosure or original record, but cannot be considered as a new content not disclosed or expected by the specification, unless those skilled in the art believe that the combination is obviously unfeasible. All features disclosed by the specification can be combined arbitrarily, and the combination should be understood as being disclosed by the present invention, unless those skilled in the art believe that the combination is obviously unreasonable. The numerical points disclosed by the specification comprise not only the specifically mentioned individual numbers, but also the terminals of each numerical ranges, while any of the ranges formed by the combination of the numerical points should be deemed as being disclosed or recorded by the specification, regardless of the numerical pairs of the lower and upper limits of the ranges being disclosed one by one specifically or not.

(I) A Process of Cultivating Microalgae

The present invention provides a process of cultivating microalgae, wherein in the nutrient stream for cultivating microalgae, at least one of the nitrogen source, phosphorus source and carbon source is provided in the form of a nutrient salt, wherein during the cultivation, the pH of the microalgae suspension is adjusted with nitric acid and/or nitrous acid. According to the present invention, the cultivation may be a photoautotrophic cultivation (under illumination, using only an inorganic carbon source, such as $CO_2$, for growth), a heterotrophic cultivation (using only an organic carbon source for growth) or a mixotrophic cultivation (under illumination simultaneously with using an inorganic carbon source, such as $CO_2$, and an organic carbon source for growth). The growth of microalgae needs essential conditions, for example, a suitable temperature for the microalgae suspension, sufficient illumination (photoautotrophic or mixotrophic cultivation), sufficient water, $CO_2$, and nutrient substance provided in the form of a nutrient solution, such as nitrogenous fertilizer, phosphate fertilizer and the like, and controlling the dissolved oxygen and pH of the microalgae suspension within appropriate ranges. Although these conditions may vary from microalgae to microalgae, the conditions are known in the art. Generally, culture is carried out at a temperature of 15-40° C., preferably 25-35° C.; and the microalgae suspension has a pH of 6-11, preferably 7-9. For a photoautotrophic cultivation or a mixotrophic cultivation, a useful illumination intensity is 1000-200000 lux, preferably 5000-150000 lux. The inventors has discovered, through abundant study and experiments, that when microalgae metabolizes any one of an alkali nitrate, an alkali nitrite, an alkali carbonate, an alkali bicarbonate, an alkali phosphate and an alkali biphosphate, or a combination thereof, the pH of the microalgae suspension increases without adding $CO_2$ or a pH regulator into the microalgae suspension during the microalgae cultivation. In particular, when microalgae metabolizes an alkali nitrate, an alkali nitrite or a combination thereof, the pH of the microalgae suspension increases rapidly. Microalgae is generally cultivated at a pH of 6-11. When the culture medium contains a nutrient substance above, nitric acid and/or nitrous acid is preferably used to adjust the pH of the microalgae suspension in order to avoid the pH of the culture medium beyond the range allowed by the growth of microalgae. The present invention has not any special restriction on the category of microalgae. A microalgae with high lipid content is preferably cultivated according to the present invention, which can not only produce a biological energy sources, but also reduce the waste gas pollution. Although the cost of heterotrophic or mixotrophic cultivation may be increased partly due to the use of an organic carbon source, the biomass productivity thereof is increased significantly. Accordingly, the subsequent processing procedures can be simplified. If an aseptic cultivation can be avoided, a rigorous sterilization to the system consuming abundant of steam can be avoided, so as to reduce significantly the cultivation cost. According to the present invention, it is especially preferable to use microalgae adaptable to heterotrophic or mixotrophic cultivation, such as *Chlorella* sp., *Scenedesmus* sp., *Spirulina* sp. or *Monoraphidium* sp. Surprisingly, when these categories of microalgae are cultured by heterotrophic or mixotrophic cultivation, once a certain quantity of EM bacteria is added, the cultivation can be conducted successfully even without sterilization. The growth rate of microalgae is accelerated greatly. Even if water source contains abundant of harmful bacteria and/or the cultivation is carried out at an open place without sealing, the result in similarly positive. As compared, without adding the EM bacteria, a heterotrophic or mixotrophic cultivation generally fails. According to the present invention, a heterotrophic or mixotrophic cultivation is conducted with the addition of EM bacteria, preferably without sterilization or the addition of a bactericide. EM bacteria (Effective Microorganisms) is known, which consists essentially of tens of microorganism belonging to photosynthetic bacteria, *lactobacillus*, microzyme, Gram-positive actinomyce, and filamentous. EM bacteria can be formulated according to the teaching from prior art, or can be obtained commercially, and be fermented according to the teaching from prior art or the specification of the commercial formulation before use. According to the present invention, the amount of EM bacteria should satisfy the need of facilitating the growth of microalgae. The amount of EM bacteria cannot be either too few to be effective, or too many to consume excessive nutrient substances due to the competition thereof with microalgae. Any way of adding EM bacteria (such as an one-time addition or a batched addition) and any amount of EM bacteria are useful, as long as the growth of microalgae can be facilitated. According to the present invention, EM bacteria is added in an amount of $1 \times 10^5$ cells/L microalgae suspension-$9 \times 10^8$ cells/L microalgae suspension, preferably is $1 \times 10^6$ cells/L microalgae suspension-$5 \times 10^8$ cells/L microalgae suspension, further preferably is $1 \times 10^6$ cells/L microalgae suspension-1×10⁸ cells/L microalgae suspension. According to the present invention, when a microalgae is cultured by heterotrophic or mixotrophic cultivation, the useful organic carbon source includes, but not limited to, at least one of sugar, organic acid, salt of an organic acid, alcohol, cellulose hydrolyzate and glucidtemns; such as at least one of glucose, levulose, acetic acid, sodium acetate, lactic acid, ethanol, methanol and cellulose hydrolyzate, preferably glucose. According to the increasing profile of the biomass of microalgae and the consuming profile of the nutrient substance in the culture medium, the consumed nutrient substance should be supplemented in time. According to the present invention, the nutrient substance can be supplemented in any ways, such as a supplement in batches or a continuous supplement, as long as the amount of the nutrient substance added is controlled within an appropriate range. According to the present invention, for heterotrophic or a mixotrophic cultivation, the concentration of an organic carbon source is generally controlled at 1 g/L microalgae suspension-30 g/L microalgae suspension, preferably 2 g/L microalgae suspension-10 g/L microalgae suspension. The organic carbon source may be added by an one-time addition or a batched addition. According to the present invention, in the alkali nutrient salt, the metal ion is sodium and/or potassium. According to the present invention, the nitrogen source is preferably an alkali nitrate and/or an alkali nitrite. According to the present invention, the phosphorus source is preferably an alkali phosphate and/or an alkali biphosphate. According to the present invention, a part of the carbon source can be an alkali carbonate and/or an alkali bicarbonate. According to the present invention, when a photoautotrophic cultivation is used, all or most of the carbon source is provided in the form of $CO_2$. According to the present invention, the amount of the nitrogen source, phosphorus source, or carbon source is provided as known in the art, for example, the amount of nitrogen source, calculated as nitrogen atoms, is 0.1-400 mmol/L, preferably is 10-300 mmol/L, still further preferably is 20-200 mmol/L. The process according to the present invention further comprises separating a microalgae biomass from the microalgae suspension, and recycling a residual cultivation solution obtained through the separation of the microalgae biomass to cultivate microalgae. (II) A joint method of cultivating microalgae and denitrating an industrial waste gas The present invention provides a joint method of cultivating microalgae and denitrating an industrial waste gas, comprising the steps of:

(1) a cultivation step of cultivating microalgae;
(2) a separation step of separating a microalgae suspension obtained from step (1) into a wet microalgae (microalgae biomass) and a residual cultivation solution;
(3) a NOx immobilizing step of denitrating an industrial waste gas with the residual cultivation solution obtained from step (2); and
(4) optionally, a drying step of drying the microalgae biomass obtained from step (2) to provide a microalgae product;
wherein the NOx immobilized nutrient stream obtained from step (3) is used to provide nitrogen source to the microalgae cultivation of step (1). The step (3) above can be conducted by various ways. The prior art deems that nitrate is capable of being used as the nitrogen source for the microalgae cultivation. However, under certain situations, the accumulation of metal ion contained in the nitrate may probably inhibit the growth of microalgae. Therefore, in one preferable embodiment, the joint method according to the present invention involves an acid procedure, wherein the step (3) comprises:

(i) a sub-step of converting NOx in the industrial waste gas into nitric acid and/or nitrous acid; and
(ii) mixing the residual cultivation solution obtained from step (2) with the nitric acid and/or nitrous acid (preferably the nitric acid and optionally the nitrous acid) obtained from step (i), so as to achieve denitration of the industrial waste gas. In the embodiment, the solution obtained from mixing is used as the NOx immobilized nutrient stream to provide nitrogen source to the microalgae cultivation in step (1). In another preferable embodiment, the joint method involves an alkali procedure, wherein the step (3) comprises:
(i') immobilizing NOx in the industrial waste gas directly with the residual cultivation solution obtained from step (2). In the embodiment, the NOx immobilized nutrient stream is used to provide nitrogen source to the microalgae cultivation. Step (1) can be carried out using any specific embodiment in the portion of "a process of cultivating microalgae" above, and the features, steps, conditions or a combination thereof are useful. According to the present invention, the NOx content in the industrial waste gas is not specifically restricted. In general, the NOx content in an industrial waste gas is from several hundred ppm (volume) to several thousand ppm, for example, from 100 ppm to 5000 ppm. According to the present invention, in the industrial waste gas to be treated, the molar fraction of NO, based on the total amount of NOx, is ≥80%. Further, in the industrial waste gas, the molar fraction of NO, based on the total amount of NOx, is ≥90%. According to the present invention, in the acid procedure, any known process can be used in step (i) to convert NOx in the industrial waste gas into nitric acid and/or nitrous acid. Some categories of microalgae cannot metabolize $NO_2^-$. When cultivating these categories of microalgae, it is needed to select an appropriate process for immobilizing NOx, so as to convert most or all of NOx into $NO_3^-$. According to the present invention, any process known to be appropriate is useful, such as an oxidation absorption process using nitric acid/hydrogen peroxide as an absorbent. According to the present invention, it is preferable to cultivate a microalgae capable of metabolizing both $NO_3^-$ and $NO_2^-$, such as the *Chlorella* sp., *Monoraphidium* sp., *Scenedesmus* sp. or *Spirulina* sp. selected by the present invention, where the problem of converting to $NO_2^-$ is substantially avoided. Considering that the nitrogen source is consumed rapidly in some circumstances of microalgae cultivation, an acid procedure is preferably used for heterotrophic cultivation, and/or an acid procedure is preferably used for *Spirulina* sp. cultivation. According to the present invention, in one embodiment, a wet denitration is preferably used in step (i) to convert NOx in the industrial waste gas into nitric acid and. The absorption solution used to absorb NOx in the wet denitration consists of 0.5 m %-58 m % of nitric acid, 0.001 m %-25 m % of hydrogen peroxide and balance of water. Such an embodiment is thus called as an acid procedure involved joint method. The inventors have found by research that regarding an acid procedure involved joint method, although an aqueous solution either having a high concentration of nitric acid/a low concentration of hydrogen peroxide or an aqueous solution having a high concentration of hydrogen peroxide/a low concentration of nitric acid can absorb effectively NOx with low oxidizability, the two methods may both have the defect of a rapid decomposition and a great dissipation of hydrogen peroxide. In an aqueous solution having a low concentration of hydrogen peroxide/a low concentration of nitric acid, the decomposition of hydrogen peroxide is relatively slow whilst the aqueous solution having a low concentration of hydrogen peroxide/a low concentration of nitric acid has a very low absorbing activity on NOx with low oxidizability. The inventors have discovered surprisingly by deep study that although the aqueous solution having a low concentration of hydrogen peroxide/a low concentration of nitric acid shows a very low activity of absorbing NOx with low oxidizability at the initial stage of cultivation, the absorbing activity on NOx with low oxidizability of the aqueous solution increases gradually. After a period (activating stage), the absorbing activity on NOx with low oxidizability of the aqueous solution reaches a stable stage at a high level. Therefore, preferably, in one embodiment, the absorption solution having a low concentration of hydrogen peroxide/a low concentration of nitric acid according to the present invention is subjected to an activating stage before the use for absorbing NOx. According to the present invention, in the aforementioned wet denitration, the absorption solution consists preferably of 10 m %-25 m % of nitric acid, 0.1 m %-1 m % of hydrogen peroxide and balance of water; more preferably 10 m %-25 m % of nitric acid, 0.2 m %-1 m % of hydrogen peroxide and balance of water. As stated above, the absorption solution having such a composition has a very low denitration activity, which absorption solution can satisfy the requirement by the denitration of an industrial waste gas only after an activating stage. The activating stage comprises: contacting a solution consisting of 10 m %-25 m % of nitric acid, 0.1 m %-1 m % of hydrogen peroxide and balance of water with a NOx-containing gas, until the denitrating activity of the solution does not increase any more, which means the activating step being completed. In the NOx-containing gas, NO occupies a molar fraction, based on the total amount of NOx, of ≥80%. The NOx-containing gas used for activating the absorption solution can be said industrial waste gas. According to the present invention, in the aforementioned wet denitration, the denitration can be conducted at a temperature from −10° C. to 40° C., and a pressure of 0.1 Mpa-1 Mpa; preferably at room temperature (10° C.-40° C.) and atmospheric pressure. According to the present invention, in the wet denitration above, there is not special restriction on the contacting way for the contact between the industrial waste gas and the active absorption solution, such as any one of the following (A), (B), (C) or a combination thereof: (A) dispersing the industrial waste gas as bubbles in the absorption solution; (B) dispersing the absorption solution as liquid drops in the industrial waste gas; (C) contacting liquid with the industrial waste gas in the form of a film-like movement. The way (A) is preferably used. According to the present invention, in the wet denitration, one absorption column or more absorption columns in series can be used; preferably one absorption column or 2-3 absorption columns in series. There is not special restriction on the form of the absorption column, such as one or a combination of the followings: a tray absorption column, a bubble absorption column, a stirring bubble absorption column, a spray column dispersing the absorption solution as liquid drops in a gas phase, a packed absorption column and a falling film absorption column; preferably a bubble absorption column or a stirring bubble absorption column. When an alkali procedure or an acid procedure is involved, it is preferable to adjust the pH of the culture medium by microalgae metabolism in step (1), such that the residual cultivation solution obtained from step (2) has a pH>8, more preferably a pH of 9-11. As stated above, when the culture medium of microalgae contains one of alkali nitrate, alkali nitrite, alkali carbonate, alkali bicarbonate, alkali phosphate and alkali biphosphate or a combination thereof, the pH of the microalgae suspension increases if no or less $CO_2$ (or a pH regulator) is provided. Using this phenomena, no or less $CO_2$ (or a pH regulator) can be provided at the late stage during the microalgae cultivation, but causes the microalgae suspension to be alkaline at the terminal of cultivation through metabolism of the microalgae instead. Accordingly, the residual cultivation solution can be separated from the microalgae cultivation to immobilize NOx in the waste gas or to neutralize the acid liquid after immobilizing NOx, which is subsequently used to in turn provide the essential nitrogen source to the microalgae cultivation. Therefore, in one embodiment, the pH of the residual cultivation solution is controlled, by adjusting the amount of $CO_2$ supplied to the microalgae cultivation, to be >8, more preferably 9-11. The inventors have found that the alkaline residual cultivation solution after the separation of microalgae can immobilize NOx in a waste gas or to neutralize the acid liquid after immobilizing NOx with a high efficiency, so as to obtain a solution containing $NO_3^-$ and/or $NO_2^-$, which solution may be subsequently used to provide directly nitrogen source to a followed batch of microalgae cultivation. After the metabolism of the nitrogen source by microalgae, the followed batch of microalgae suspension becomes alkaline again. As such, a closed recycle is established between the culture medium of a microalgae cultivation and the absorption solution or neutralization solution of an industrial waste gas denitration, so as to combine synthetically a "microalgae cultivation" and an "industrial waste gas denitration", which can not only convert the nitrogen pollutant into a useful biomass through microalgae effectively, but also maintain the "microalgae cultivation" and the "waste gas denitration" as two relatively independent processes, avoiding any unfavorable interaction therebetween. An absorption/immobilization process by alkaline solution is known in the art for the denitration of a waste gas. There are a great deal of researches about absorbing/immobilizing NOx of waste gas with an alkaline aqueous solution. The present invention can use any one of the known processes. As known in the art, in order to immobilize NO completely, an oxidation column is added before an alkaline solution absorption column, which oxidizes NO to $NO_2$ with the oxygen remained in the waste gas or by adding ozone, so as to provide an optimal oxidizability (a molar ratio of $NO_2/NO$) to the alkaline solution immobilization process. Catalytically oxidizing catalysts useful for various cases are known in the art. For example, active carbon, active carbon fiber, high silica Na-ZSM-5 molecular sieve or pure silica β molecular sieve can be used as a catalyst to oxidize NO into $NO_2$ at room temperature. According to the present invention, step (i') uses an alkaline solution absorption process to absorb/immobilize NOx, where a residual cultivation solution obtained from the microalgae cultivation is used as an absorption solution for absorbing/immobilizing NOx of a waste gas. It is noted that a step of extracting nitrate according to the conventional alkaline solution immobilization process is omitted. Rather, the solution obtained after the immobilization of NOx is used directly to provide nitrogen source to the microalgae cultivation according to the present invention. According to the present invention, it is preferable to cultivate microalgae capable of metabolizing both $NO_3^-$ and $NO_2^-$, such as the *Chlorella* sp., *Monoraphidium* sp., *Scenedesmus* sp. or *Spirulina* sp. selected by the present invention. According to the present invention, a microalgae resistant to a high alkaline environment is preferred, where the pH of the residual cultivation solution to cultivate such a microalgae can be further increased, so as to increase the efficiency of the reaction thereof with nitric acid and/or nitrous acid or of NOx immobilization. The inventors have selected out, by abundant of tests, a microalgae resistant to a highly alkaline environment, such as *Chlorella* sp., *Monoraphidium* sp., *Scenedesmus* sp. or *Spirulina* sp., which microalgae can grow healthily at a pH of 9-11. According to the present invention, a microalgae capable of increasing rapidly the pH of the microalgae suspension through the metabolism itself without addition of $CO_2$ is preferred, where the efficiency of microalgae cultivation can be further increased by cultivating such a microalgae. The inventors have selected out, by abundant of tests, microalgaes capable of increasing rapidly the pH of the microalgae suspension, such as *Chlorella* sp., *Monoraphidium* sp., *Scenedesmus* sp. or *Spirulina* sp., which microalgaes can increase the pH of the microalgae suspension to be 9-11 within 1-24 hours, allowing the microalgae suspension reacting with nitric acid and/or nitrous acid or absorbing/immobilizing NOx with a high efficiency. Preferably, in the NOx immobilized nutrient stream obtained from step (i') to provide nitrogen source to the microalgae, the amount of the nitrogen-containing compound, calculated as nitrogen atoms, is 0.1-400 mmol/L, preferably 10-300 mmol/L, still further preferably 20-200 mmol/L. In addition to NOx, an industrial waste gas may also contain other pollutants, such as SOx. Those skilled in the art can determine, through a simple test (for example, through measuring the immobilizing rate of NOx or measuring the varied growth rate of microalgae), whether a waste gas comprises, even in an excessive amount of, a pollutant significantly damaging the joint method according to the present invention. The inventors have discovered that when the flue gas from an industrial discharge contains a high content of SOx, the efficiency of immobilizing NOx by the residual cultivation solution may be reduced. As required, those skilled in the art can reduce the SOx in a waste gas to a level not damaging significantly the joint method according to the present invention by a conventional technic means. A flue gas from general industry discharge, especially a coal flue gas, contains abundant of SOx. Therefore, regarding such an industrial waste gas, SOx contained in the industrial waste gas should be removed before denitrating the waste gas. According to the present invention, the industrial waste gas is free of SOx or has been desulfurized (removed with of SOx in the waste gas). It should be understood that the "microalgae cultivation" and "industrial waste gas denitration" involved in the present invention are two relatively independent processes. The $CO_2$-containing gas is used mainly to provide carbon source to the microalgae growth, which gas is free substantially of SOx or NOx. The $CO_2$-containing gas may be a purified industrial waste gas (removed with SOx and NOx in the waste gas), or an industrial waste gas free of SOx and NOx. The present invention establishes a cyclic economic pattern of reducing the discharge of pollutant from an industrial waste gas and producing a microalgae biomass. NOx in a waste gas from an industrial discharge is used as nitrogen source for the nutrient stream, which not only reduces the pollutant discharge, but also provides a valuable microalgae biomass. In such a cyclic economic pattern, a part of the cost for treating an industrial waste gas is recovered by the microalgae cultivation, and the discharge of waste gas and waste water, as well as the environmental pollution, by industry are reduced. A closed recycle is thus formed, where only a microalgae biomass is obtained at the outlet. The joint method according to the present invention can also be further associated with an additional microalgae cultivation.

Figure 13:
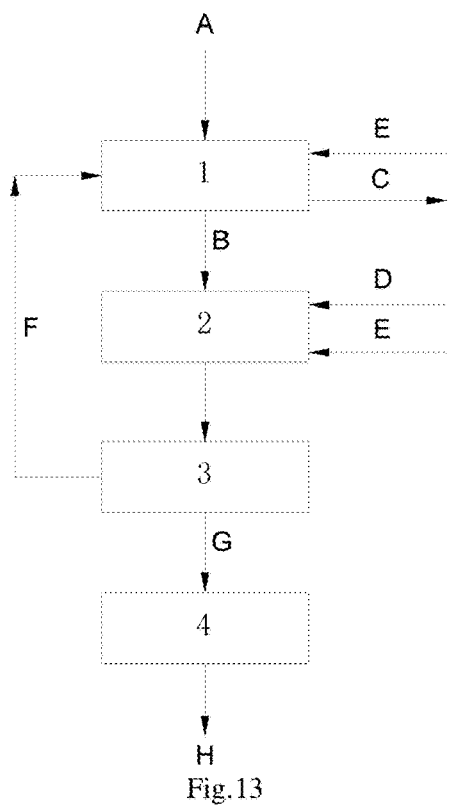
FIG. 13 represents a general flow chart showing a joint method according to the present invention.

For instance, a microalgae is provided at the initial stage of a joint method, and in particular, additional microalgaes are provided when the microalgae in the joint method above needs supplement. The additional microalgae cultivation can be a separate process independent from the steps of the microalgae cultivation of the joint method, so as to input microalgae to, for example, the microalgae cultivating device as needed, see, for example, FIG. 15. The additional microalgae cultivation can also be incorporated into the joint method, e.g., downstream the microalgae cultivation steps stated above. The additional microalgae cultivation can be a photoautotrophic cultivation, a mixotrophic cultivation and/ or a heterotrophic cultivation, as long as the amount of microalgae generated satisfies the need of supplementing the joint method. In one embodiment, the additional microalgae cultivation is a photoautotrophic cultivation, carried out by any known process in the art, see, for example, the process showed by FIG. 15. The invention has been illustrated by example of the joint method involving a NOx-containing industrial waste gas and a microalgae cultivation, whilst those skilled in the art will understand that the joint method is also useful for any other NOx-containing gas requiring denitration, as long as the gas is compatible with the microalgae cultivation. (III) A system used for the joint method of cultivating microalgae and denitrating industrial waste gas The present invention provides a system useful for the joint method of cultivating microalgae and denitrating industrial waste gas, comprising, optionally from upstream to downstream:

a NOx immobilizing unit, having an inlet for a NOx-containing industrial waste gas, an inlet for a residual cultivation solution, an outlet for a NOx immobilized nutrient stream and an outlet for a purified industrial waste gas, and optionally an inlet for a nutrient solution, useful for denitration and providing the NOx immobilized nutrient stream;

a microalgae cultivating device, having an inlet for the NOx immobilized nutrient stream, an inlet for a microalgae strain and an outlet for a microalgae suspension, and optionally an inlet for a nutrient solution, optionally an inlet for EM bacteria, useful for microalgae cultivation using the NOx immobilized nutrient stream;

a separator, having an inlet for the microalgae suspension, an outlet for a microalgae biomass and an outlet for the residual cultivation solution, useful for separating the microalgae suspension obtained from the microalgae cultivating device into the microalgae biomass and the residual cultivation solution; and a recycle line, linking the outlet for the residual cultivation solution of the separator to the inlet for the residual cultivation solution of the NOx immobilizing unit;

and optionally, a dryer, useful for drying the microalgae biomass to provide a microalgae product. Preferably, for a joint method involving the acid procedure, the NOx immobilizing unit has an inlet for the nutrient solution. Preferably, for a joint method involving the alkali procedure, the microalgae cultivating device has an inlet for the nutrient solution. In one preferable embodiment, the joint method involves the acid procedure, wherein the NOx immobilizing unit comprises a denitration reactor and a NOx immobilizing nutrient stream formulating device. In one preferable embodiment, the joint method involves the alkali procedure, wherein the NOx immobilizing unit is a denitration reactor. Referring to FIG. 13, an embodiment of the system according to the present invention comprises:

NOx immobilizing unit 1; microalgae cultivating device 2; separator 3; and dryer 4. Regarding an acid procedure, NOx immobilizing unit 1 comprises: denitration reactor 1-1; and NOx immobilizing nutrient stream formulating device 1-2 (referring to FIG. 14); while regarding an alkali procedure, 1 is 1-1: denitration reactor. Thus in the system, a NOx-containing gas A, a residual cultivation solution F from separator 3 and optionally a nutrient solution E is fed into NOx immobilizing unit 1, and a NOx immobilized nutrient stream B and a purified gas C are obtained after treatment; subsequently, the NOx immobilized nutrient stream B from NOx immobilizing unit 1, a microalgae strain D and optionally a nutrient solution E are fed into microalgae cultivating device 2; a microalgae suspension from the cultivation is fed into separator 3 and separated therein to provide a wet microalgae (microalgae biomass) G and a residual cultivation solution F; and the microalgae biomass G is fed into dryer 4, where it is dried to provide a microalgae product H. Preferably, for an acid procedure, the nutrient solution E is added into NOx immobilizing unit 1. Preferably, for an alkali procedure, the nutrient solution E is added into microalgae cultivating device 2.

Figure 14:
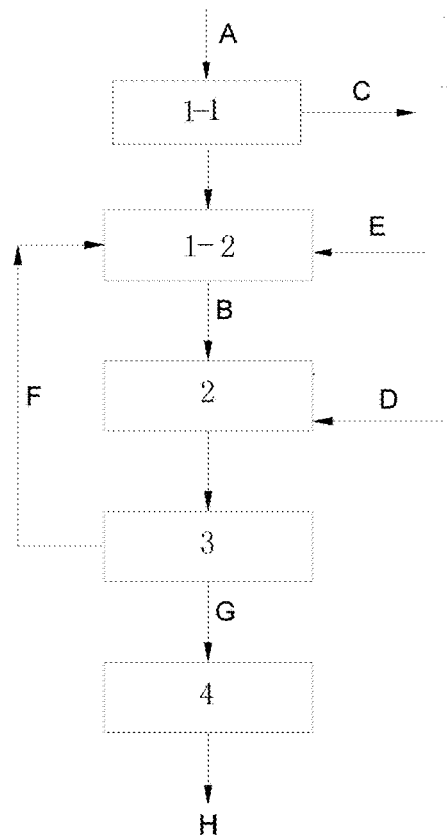
FIG. 14 represents a flow chart showing a joint method involving an acid procedure according to the present invention.

FIG. 14 exemplifies an acid procedure conforming to the embodiment of FIG. 13. As stated above, for an acid procedure, NOx immobilizing unit 1 consists of denitration reactor 1-1 and NOx immobilizing nutrient stream formulating device 1-2. Accordingly, regarding NOx immobilizing unit 1, a NOx-containing gas A and an aqueous solution having a low concentration of hydrogen peroxide/a low concentration of nitric acid used as a NOx immobilizing solution (not shown in the figure) is fed into denitration reactor 1-1, where a NOx immobilized nutrient stream and a purified gas C are obtained after treatment; the NOx immobilized nutrient stream, and a residual cultivation solution F from separator 3 and nutrient solution E is fed into NOx immobilizing unit 1, where a NOx immobilized nutrient stream B is obtained after treatment. The other facilities and processing procedures are same as the general embodiment showed by FIG. 13.

Figure 15:
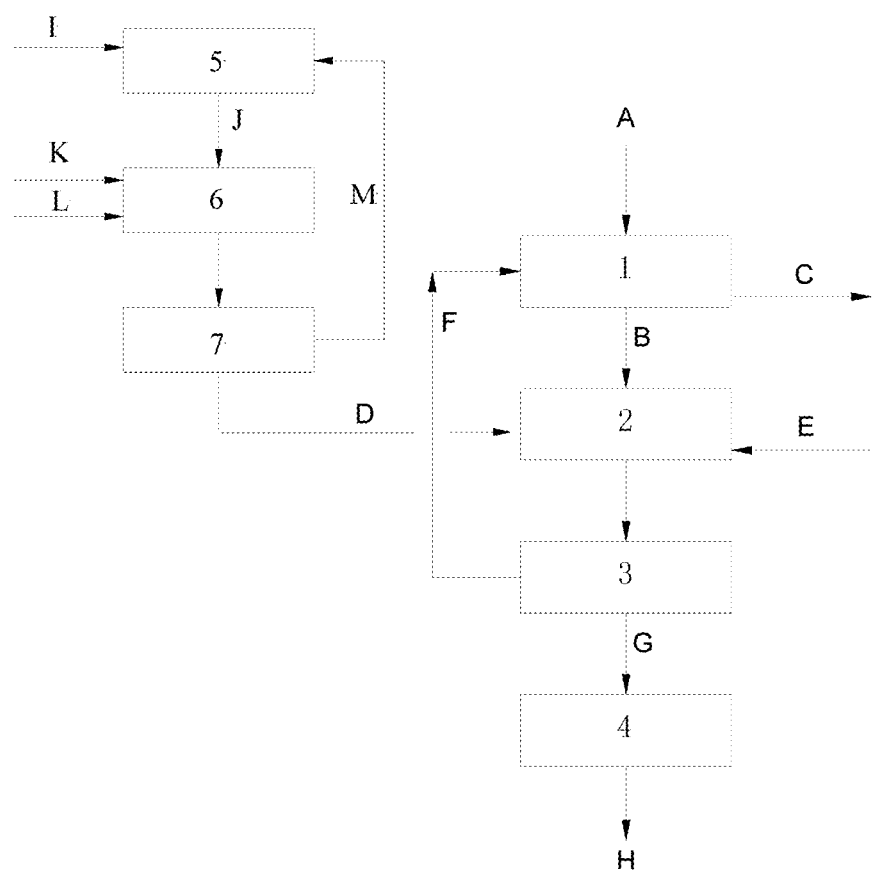
FIG. 15 represents a flow chart showing a joint method involving an acid procedure combined with an additional photoautotrophic cultivation according to the present invention. In these figures.

FIG. 15 instantiates a combination of the joint method according to the present invention with an additional microalgae cultivation. In the combined process, the joint method according to the present invention has processing procedures as showed by FIG. 13, except that the microalgae strain D fed to microalgae cultivating device 2 comes specifically from an additional microalgae cultivation process, which is a photoautotrophic cultivation. The additional microalgae cultivation provides microalgae to the joint method at the initial stage, in particular providing additional microalgaes when the microalgae in the joint method above needs supplement. In the combined process showed by FIG. 15, the additional microalgae cultivation can be a separate process independent from the steps of the microalgae cultivation of the joint method, so as to input microalgae to, for example, the microalgae cultivating device as needed According to the discussion above, the present invention provides in one aspect the following embodiments:

1. A process of cultivating microalgae, characterized in that, during the microalgae cultivation, EM bacteria is added into the microalgae suspension.

2. The process according to embodiment 1, characterized in that the microalgae is a heterotrophic or mixotrophic microalgae.

3. The process according to embodiment 2, characterized in that the microalgae is selected from the group consisting of Cyanophyta and Chlorophyta.

4. The process according to embodiment 2, characterized in that the microalgae is *Chlorella* sp., *Scenedesmus* sp., *Monoraphidium* sp. or *Spirulina* sp.

5. The process according to embodiment 2, characterized in that the organic carbon source used is at least one selected from the group consisting of sugar, organic acid, salt of an organic acid, alcohol, cellulose hydrolyzate and glucidtemns; preferably at least one of glucose, levulose, acetic acid, sodium acetate, lactic acid, ethanol, methanol and cellulose hydrolyzate, more preferably glucose.

6. The process according to embodiment 2 or 3, characterized in that the concentration of the organic carbon source used is generally controlled at 1 g/L microalgae suspension-30 g/L microalgae suspension, preferably 2 g/L microalgae suspension-10 g/L microalgae suspension.

7. The process according to any one of embodiments 1-6, EM bacteria is added in an amount of $1 \times 10^5$ cells/L microalgae suspension-$9 \times 10^8$ cells/L microalgae suspension, preferably is $1 \times 10^6$ cells/L microalgae suspension-$5 \times 10^8$ cells/L microalgae suspension, further preferably is $1 \times 10^6$ cells/L microalgae suspension-$1 \times 10^8$ cells/L microalgae suspension.

8. The process according to any one of embodiments 1-7, characterized in that the cultivation is conducted at a temperature of 15-40° C., and the microalgae suspension has a pH of 6-11.

9. The process according to any one of embodiments 1-8, characterized in that when the cultivation is a photoautotrophic cultivation or a mixotrophic cultivation, the illumination intensity is 1000-200000 lux.

10. The process according to any one of embodiments 1-9, characterized in that during the cultivation, $NO_3^-$ and/or $NO_2^-$ are used as nitrogen source, preferably a nitrate and/or a nitrite obtained from the denitration of an industrial waste gas being used as nitrogen source.

11. The process according to any one of embodiments 1-10, wherein in the nutrient stream for cultivating microalgae, at least one of the nitrogen source, phosphorus source and carbon source is provided in the form of a nutrient salt, characterized in that during the culture, the pH of the microalgae suspension is adjusted with nitric acid and/or nitrous acid.

12. The process according to any one of embodiments 1-11, characterized in that the nitric acid is obtained by converting NOx in an industrial waste gas into nitric acid through a wet denitration; and the absorption solution used in the wet denitration consists of 0.5 m %-58 m % of nitric acid, preferably 10 m %-25 m % of nitric acid, 0.001 m %-25 m % of hydrogen peroxide, preferably 0.1 m %-1 m % of hydrogen peroxide, and balance of water.

13. A joint method of cultivating microalgae and denitrating an industrial waste gas, comprising the steps of:
(1) a cultivation step of cultivating microalgae;
(2) a separation step of separating a microalgae suspension obtained from step (1) into a wet microalgae (microalgae biomass) and a residual cultivation solution;
(3) a NOx immobilizing step of denitrating the industrial waste gas with the residual cultivation solution obtained from step (2); and
(4) optionally, a drying step of drying the microalgae biomass obtained from step (2) to provide a microalgae product;

wherein a NOx immobilized nutrient stream obtained from step (3) is used to provide nitrogen source to the microalgae cultivation of step (1).

14. The joint method according to embodiment 13, characterized in that the step (1) of cultivating microalgae is carried out using a process according to any one of embodiments 1-12.

15. The joint method according to embodiment 13 or 14, characterized in that the joint method involves an acid procedure, wherein the step (3) comprises:
(i) a sub-step of converting NOx in the industrial waste gas into nitric acid and/or nitrous acid; and
(ii) mixing the residual cultivation solution obtained from step (2) with the nitric acid and/or nitrous acid obtained from step (i), so as to achieve denitration of the industrial waste gas.

16. The joint method according to embodiment 13 or 14, characterized in that the joint method involves an alkali procedure, wherein the step (3) comprises:
(i') immobilizing NOx in the industrial waste gas directly with the residual cultivation solution obtained from step (2).

17. The method according to any one of embodiments 13-16, characterized in that when the cultivation is a photoautotrophic cultivation or a mixotrophic cultivation, a $CO_2$-containing gas is used as an inorganic carbon source, preferably the $CO_2$-containing gas being an purified industrial waste gas or an industrial waste gas free of SOx and NOx.

18. The method according to any one of embodiments 13-17, characterized in that in the NOx immobilized nutrient stream, the amount of the nitrogen-containing compound, calculated as nitrogen atoms, is 0.1-400 mmol/L, preferably 10-300 mmol/L, still further preferably 20-200 mmol/L.

19. The method according to any one of embodiments 13-18, characterized in that the industrial waste gas is free of SOx or is desulfurized.

20. The method according to any one of embodiments 13-19, characterized in that during the late stage of the microalgae cultivation, no or less $CO_2$ or a pH regulator is provided, while the microalgae suspension is led to be alkaline at the end of cultivation through the microalgae metabolism; wherein the alkali nutrient salt is any one of an alkali nitrate, an alkali nitrite, an alkali carbonate, an alkali bicarbonate, an alkali phosphate and an alkali biphosphate, or a combination thereof, preferably an alkali nitrate and/or an alkali nitrite.

In another aspect, the present invention provides the following embodiments:

1. A process of cultivating microalgae, wherein in the nutrient stream for cultivating microalgae, at least one of the nitrogen source, phosphorus source and carbon source is provided in the form of a nutrient salt, characterized in that during the cultivation, the pH of the microalgae suspension is adjusted with nitric acid and/or nitrous acid.

2. The process according to embodiment 1, characterized in that, during the cultivation, EM bacteria is added into the microalgae suspension.

3. The process according to embodiment 2, characterized in that EM bacteria is added in an amount of $1\times10^5$ cells/L microalgae suspension-$9\times10^8$ cells/L microalgae suspension, preferably is $1\times10^6$ cells/L microalgae suspension-$5\times10^8$ cells/L microalgae suspension, further preferably is $1\times10^6$ cells/L microalgae suspension-$1\times10^8$ cells/L microalgae suspension.

4. The process according to any one of embodiments 1-3, characterized in that the microalgae is a heterotrophic or mixotrophic microalgae.

5. The process according to any one of embodiments 1-4, characterized in that the microalgae is a Cyanophyta or a Chlorophyta, preferably *Chlorella* sp., *Scenedesmus* sp., *Monoraphidium* sp. or *Spirulina* sp.

6. The process according to any one of embodiments 1-5, characterized in that the nitric acid is obtained by converting NOx in an industrial waste gas into nitric acid through a wet denitration; and the absorption solution used in the wet denitration consists of 0.5 m %-58 m % of nitric acid, preferably 10 m %-25 m % of nitric acid, 0.001 m %-25 m % of hydrogen peroxide, preferably 0.1 m %-1 m % of hydrogen peroxide, and balance of water.

7. The process according to embodiment 4, characterized in that the organic carbon source used is at least one selected from the group consisting of sugar, organic acid, salt of organic acid, alcohol, cellulose hydrolyzate and glucidtemns.

8. The process according to embodiment 4, characterized in that the organic carbon source is used at a concentration of 1 g/L microalgae suspension 30 g/L microalgae suspension.

9. The process according to embodiment 1, characterized in that when the cultivation is a photoautotrophic cultivation or a mixotrophic cultivation, the illumination intensity is 1000-200000 lux.

10. A joint method of cultivating microalgae and denitrating an industrial waste gas, comprising the steps of:
(1) a cultivation step of cultivating microalgae;
(2) a separation step of separating a microalgae suspension obtained from step (1) into a wet microalgae (microalgae biomass) and a residual cultivation solution;
(3) a NOx immobilizing step of denitrating the industrial waste gas with the residual cultivation solution obtained from step (2), comprising:
(i) a sub-step of converting NOx in the industrial waste gas into nitric acid and/or nitrous acid; and
(ii) mixing the residual cultivation solution obtained from step (2) with the nitric acid and/or nitrous acid obtained from step (i), so as to achieve denitration of the industrial waste gas;
(4) optionally, a drying step of drying the microalgae biomass obtained from step (2) to provide a microalgae product;
wherein a NOx immobilized nutrient stream obtained from step (3) is used to provide nitrogen source to the microalgae cultivation of step (1).

11. The method according to embodiment 10, characterized in that in step (2), NOx in the industrial waste gas is converted into nitric acid through a wet denitration; and the absorption solution used in the wet denitration consists of 0.5 m %-58 m % of nitric acid, preferably 10 m %-25 m % of nitric acid, 0.001 m %-25 m % of hydrogen peroxide, preferably 0.1 m %-1 m % of hydrogen peroxide, and balance of water.

12. The joint method according to embodiment 10 or 11, characterized in that the step (1) of cultivating microalgae is carried out using the process according to any one of embodiments 1-9.

13. The joint method according to any one of embodiments 10-12, characterized in that in the nutrient stream of step (1), the nitrogen source is provided in the form of an alkali nitrate and/or an alkali nitrite.

14. The joint method according to any one of embodiments 10-13, characterized in that the joint method further comprises an additional microalgae cultivation step, which provides microalgae at the initial stage of the joint method, and/or provides supplementary microalgae when the microalgae in the microalgae cultivation step (1) needs supplement.

15. The joint method according to embodiment 14, characterized in that the additional microalgae cultivation step is a separate process independent from the microalgae cultivation step (1), so as to input microalgae to the microalgae cultivation step (1) as needed 16. The joint method according to embodiment 14, characterized in that the additional microalgae cultivation step is incorporated into the joint method, and is placed upstream of the microalgae cultivation step (1).

17. A system useful for the joint method of cultivating microalgae and denitrating industrial waste gas, comprising, optionally from upstream to downstream:
- a NOx immobilizing unit, useful for carrying out the denitration and providing a NOx immobilized nutrient stream;
- a microalgae cultivating device, useful for cultivating microalgae with the NOx immobilized nutrient stream;
- a separator, useful for separating a microalgae suspension obtained from the microalgae cultivating device into a microalgae biomass and a residual cultivation solution; and
- a recycle line, useful for recycling the residual cultivation solution obtained from the separator to upstream of the process, so as to immobilize NOx in the industrial waste gas;
- and optionally, a dryer, useful for drying the microalgae biomass to provide a microalgae product.

18. The system according to embodiment 17, wherein the NOx absorbing unit has an inlet for a NOx-containing industrial waste gas, an inlet for the residual cultivation solution, an outlet for the NOx immobilized nutrient stream and an outlet for the purified industrial waste gas;
the microalgae cultivating device has an inlet for the NOx immobilized nutrient stream, an inlet for a microalgae strain and an outlet for the microalgae suspension;
the separator has an inlet for the microalgae suspension, an outlet for the microalgae biomass and an outlet for the residual cultivation solution; and
the recycle line links the outlet for the residual cultivation solution of the separator to the inlet for the residual cultivation solution of the NOx absorbing unit.

19. The system according to embodiment 18, wherein the NOx absorbing unit comprises a denitration reactor and a NOx immobilizing nutrient stream formulating device.

20. The system according to embodiment 18 or 19, characterized in that the system further comprises an additional microalgae cultivation device, which provides microalgae to the system at the initial stage of the joint method, and/or provides supplementary microalgae when the microalgae in the microalgae cultivation device needs supplement.

EXAMPLES

The present invention will be further illustrated by examples below.

Measurement of optic density of the microalgae suspension ($OD_{680}$ value): measured by a spectrophotometry, using distilled water as control, and measuring the optic absorption by the microalgae suspension at a wavelength of 680 nm, which was used as an indicator of the microalgae concentration.

Measurement of nitrogen content of a solution: using an ion chromatograph, Model ICS3000 (Dionex company, USA) to measure the $NO_3^-$ content or $NO_2^-$ content in an aqueous solution, which chromatograph was equipped with an EG40 eluent generator, an electrical conductivity detector and a chameleon chromatogram workstation; Model ionpac AS11-HC separating column (250 mm×4 mm i.d.); Model ionpac AG11 guard column (50 mm×4 mm i.d.); ASRS-ULTRA anion self-generating suppressor. Eluent: KOH solution; with a flow rate of 1 ml/min; an eluent concentration of 30 mmol/L; a feeding volume of 60 μl; a column temperature of 30° C.; a suppression current of 100 ma; an external standard method for quantifying peak area.

Count of bacteria: carried out according to the steps of:
1. Washing the sample: taking 1 ml of the sample, and washing 2-3 times with 1×PBS;
2. Separating preliminarily: centrifuging at 1000 rpm for 2 min using different centrifugal forces between microalgae and bacteria, to separate preliminarily out the microalgae (bacteria being in the supernatant, while microalgae being precipitated); and optionally repeating this step for a higher microalgae content;
3. Collecting the supernatant, wherein the quantity of microalgae in the supernatant was ignorable, centrifuging at 8000 rpm for 5 min, and disposing the supernatant;
4. Resuspending the precipitation with 500 ul of bacteria membrane permeabilizer, and reacting at room temperature for 15 min;
5. Centrifuging at 8000 rpm for 5 min, and washing the bacteria solution 2 times with 1×PBS;
6. Resuspending the bacteria by adding 100 ul 1×PBS, and adding a stock solution of 5 ul PI staining solution, for reaction at room temperature for 30 min;
7. Observing and counting the bacteria under a fluorescence microscope, wherein the maximum bacteria quantity in 4 big grids was restricted to be 1000, and when the maximum quantity was greater than 1000, diluting the bacteria solution for re-counting.
8. Calculation equation:

Bacteria density in the solution measured=counting result/4×dilution fold×4×$10^4$/ml The Main Reagents:

| Reagents used | Manufacturer |
| --- | --- |
| PI Viability Staining Solution | Cat No. FXP002, Beijing 4A Biotech Co., Ltd, China. |
| Membrane permeabilizer | Cat No. REK3004, REAL_AB company, Tianjin, China. |
| Phosphate buffer (10 × PBS, ph7.4, cell culture level, aseptic) | Cat No. REK3013, REAL_AB company, Tianjin, China. |
| Cell climbing slice | NEST |

Main Instruments:

| Instruments used | Manufacturer |
| --- | --- |
| Counting plate | Shanghai Precision Instruments, Co., Ltd., China |
| Fluorescence microscope | Olympus BX-51 |

Culture medium for microalgae: the ingredients of the culture medium were showed in Table 1-Table 5.

In the present invention, an activity of denitration denoted a molar ratio of an NOx content in an industrial waste gas after treatment to an NOx content in the industrial waste gas before treatment.

TABLE 1 culture medium BG11

| Ingredients | Composition, mg/L |
|---|---|
| K₂HPO₄•3H₂O | 40 |
| NaNO₃ | 1500 |
| Na₂CO₃ | 20 |
| MgSO₄•7H₂O | 75 |
| CaCl₂•2H₂O | 36 |
| Citric acid | 6 |
| Ferric ammonium citrate | 6 |
| Disodium EDTA | 1 |
| Trace element A5 (Table 2) | 1 |

TABLE 2 trace element A5

| Ingredients | Composition, mg/L |
|---|---|
| H₃BO₃ | 2860 |
| MnCl₂•4H₂O | 1810 |
| ZnSO₄•7H₂O | 222 |
| CuSO₄•5H₂O | 79 |
| NaMoO₄•5H₂O | 390 |
| Co(NO₃)₂•6H₂O | 50 |

TABLE 3

Z-medium

| Ingredients | composition, g/L |
|---|---|
| KH₂PO₄•3H₂O | 0.50 |
| NaNO₃ | 2.5 |
| NaHCO₃ | 16.8 |
| NaCl | 1.0 |
| MgSO₄•7H₂O | 0.20 |
| K₂SO₄ | 1.0 |
| CaCl₂•2H₂O | 0.04 |
| FeSO₄•7H₂O | 0.01 |
| Disodium EDTA | 0.08 |
| Trace element A5 (Table 2) | 1 ml |

TABLE 4 heterotrophic cultivation medium

| Ingredients | Composition, g/L |
|---|---|
| KNO₃ | 10 |
| Na₂HPO₄•12H₂O | 8.8 |
| KH₂PO₄ | 0.3 |
| MgSO₄•7H₂O | 0.2 |
| CaCl₂•2H₂O | 0.02 |
| Fe-EDTA solution | 1 ml |
| Trace element (Table 5) | 3.5 ml |
| Fe-EDTA solution: | 15 g/L and |
| FeSO₄•7H₂O | EDTA 1.4 g/L |

TABLE 5 trace element

| Ingredients | Composition, g/L |
|---|---|
| H₃BO₃ | 2.86 |
| MnCl₂•4H₂O | 0.11 |
| ZnSO₄•7H₂O | 9.22 |
| CuSO₄•5H₂O | 1.00 |
| (NH₄)₆Mo₇O₂₄•4H₂O | 0.10 |
| Co(NO₃)₂•6H₂O | 0.90 |

Example 1

The example illustrated the impact of the addition of EM bacteria on a photoautotrophic cultivation.

A BG11 medium (having nutrient ingredients according to Table 1, without sterilization) was used to cultivate *Chlorella* sp., with a temperature controlled between 20 and 30° C. Compressed air and $CO_2$ were fed for cultivation. When the microalgae suspension had a pH>10, $CO_2$ was fed, while when the microalgae suspension had a pH<7.5, the feeding of $CO_2$ was ceased. Natural sunlight was used for cultivation. The illumination intensity at daytime was controlled up to 60000 lux. The $OD_{680}$ value of the microalgae suspension was detected every day. Harvest was made after a 14 day continuous cultivation. The feeding of $CO_2$-containing mixed gas was ceased 1 day before the cultivation terminal. Then, a microalgae biomass and a residual cultivation solution were obtained through centrifugal separation. The growth curve of the microalgae was showed in FIG. 1. The two tests in FIG. 1 were substantially same, except that one of the both tests was not added with EM bacteria, whilst another was added with EM bacteria in an amount of $3.6 \times 10^6$ cells/L microalgae suspension. Regarding the test with the addition of EM bacteria, during the cultivation, the bacteria count of the microalgae suspension monitored was $<6.7 \times 10^6$/ml microalgae suspension. At the cultivation terminal, the pH of the microalgae suspension had increased naturally to 9.8. It could be seen from FIG. 1 that under photoautotrophic cultivation conditions, the addition of EM bacteria promoted the growth of microalgae.

Examples 2-5 illustrated the impact of the amount of EM bacteria added on the microalgae cultivation for a mixotrophic cultivation.

Example 2

A BG11 medium (having nutrient ingredients according to Table 1, without sterilization) was used to cultivate *Chlorella* sp., with addition of 2 g/L glucose During the culture, at a temperature controlled between 20 and 30° C. Compressed air and $CO_2$ were fed for cultivation. When the microalgae suspension had a pH>10, $CO_2$ was fed, while when the microalgae suspension had a pH<7.5, the feeding of $CO_2$ was ceased. Natural sunlight was used for cultivation. The illumination intensity at daytime was controlled up to 60000 lux. The $OD_{680}$ value of the microalgae suspension was detected every day. The growth curve of the microalgae was showed in FIG. 2. The EM was added in an amount of $3.6 \times 10^6$ cells/L microalgae suspension. During the cultivation, the bacteria count of the microalgae suspension monitored was $<8 \times 10^6$/ml microalgae suspension. Harvest was made after a 14 day continuous cultivation. The feeding of $CO_2$-containing flue gas was ceased one day before the cultivation terminal, and the pH of the microalgae suspension was allowed to increase to 9.4. Then, a microalgae biomass and a residual cultivation solution were obtained through centrifugal separation.

Example 3

The example was substantially same as example 2, except that EM was added in an amount of $1.8 \times 10^7$ cells/L microalgae suspension. After the addition of EM, during the stable state of the cultivation, the bacteria count of the microalgae suspension monitored was $<1 \times 10^7$/ml microalgae suspension. At the cultivation terminal, the pH of the microalgae suspension had increased naturally to 9.3. The growth curve of the microalgae was showed in FIG. 2.

Example 4

The example was substantially same as example 2, except that EM was added in an amount of $3.6 \times 10^7$ cells/L microalgae suspension. After the addition of EM, during the stable state of the cultivation, the bacteria count of the microalgae suspension monitored was $<2 \times 10^7$/ml microalgae suspension. At the cultivation terminal, the pH of the microalgae suspension had increased naturally to 8.9. The growth curve of the microalgae was showed in FIG. 2.

Example 5

The example was substantially same as example 2, except that EM was added in an amount of $7.2 \times 10^7$ cells/L microalgae suspension. During the cultivation, the bacteria count of the microalgae suspension monitored was $<5.8 \times 10^7$/ml microalgae suspension. At the cultivation terminal, the pH of the microalgae suspension had increased naturally to 8.7. The growth curve of the microalgae was showed in FIG. 2.

Comparative Example 1

The example was substantially same as example 2, except that no EM bacteria was added.

During the cultivation, the bacteria count of the microalgae suspension monitored was up to $1.2 \times 10^8$/ml microalgae suspension. At the cultivation terminal, the pH of the microalgae suspension had increased naturally to 7.9. The growth curve of the microalgae was showed in FIG. 2.

Figure 2:
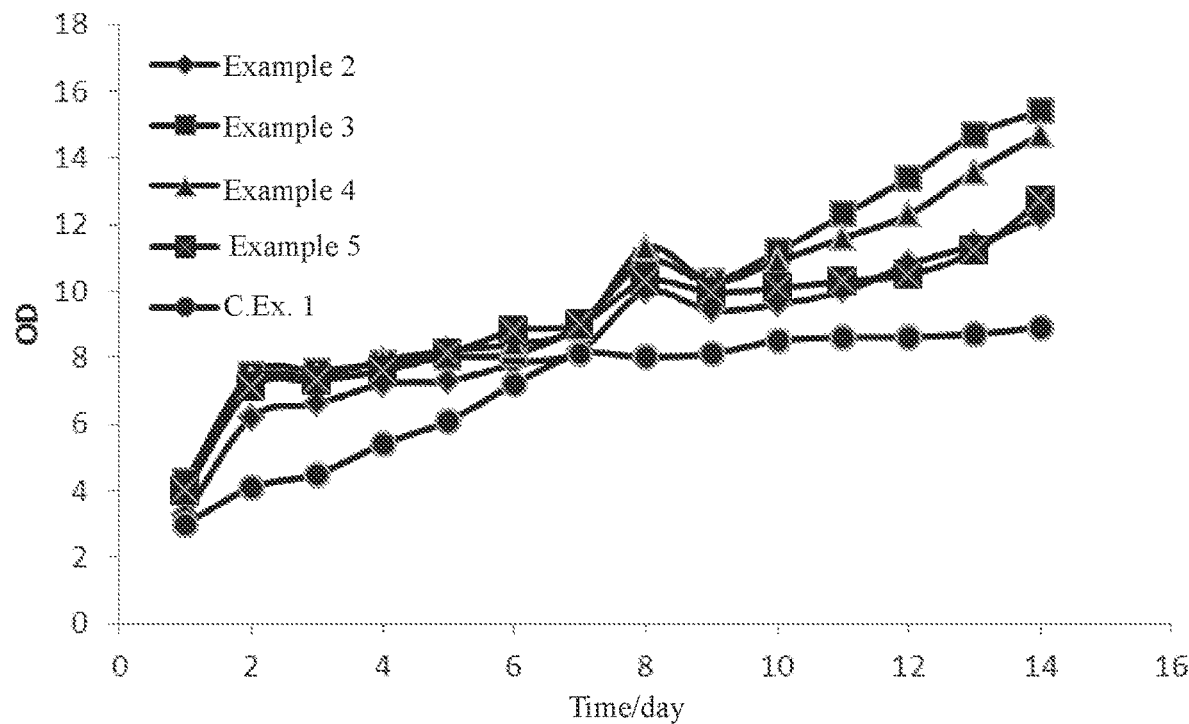
FIG. 2 represents a curve showing the growth of microalgae by mixotrophic cultivation.

It could be seen from FIG. 2 that under mixotrophic cultivation conditions, the addition of EM bacteria promoted the growth of microalgae.

Examples 6-8 illustrated the metabolism of nitrate and nitrite by microalgae.

Example 6

A BG11 medium (having nutrient ingredients according to Table 1, without sterilization) was used to cultivate *Chlorella* sp., at a temperature controlled between 20 and 30° C. Compressed air and $CO_2$ were fed for cultivation. When the microalgae suspension had a pH>10, $CO_2$ was fed, while when the microalgae suspension had a pH<7.5, the feeding of $CO_2$ was ceased. Natural sunlight was used for cultivation. The illumination intensity at daytime was controlled up to 60000 lux. The $OD_{680}$ value of the microalgae suspension was detected every day. A continuous cultivation was conducted for 14 days. The growth curve of the microalgae was showed in FIG. 3.

Example 7

The example was substantially same as example 6, except that 1.5 g/L of sodium nitrate in the medium was replaced with 1.35 g/L of sodium nitrite and 0.15 g/L of sodium nitrate. The growth curve of the microalgae was showed in FIG. 3.

Example 8

The example was substantially same as example 7, except that the microalgae cultivated was *Monoraphidium* sp. The growth curve of the microalgae was showed in FIG. 3.

Figure 3:
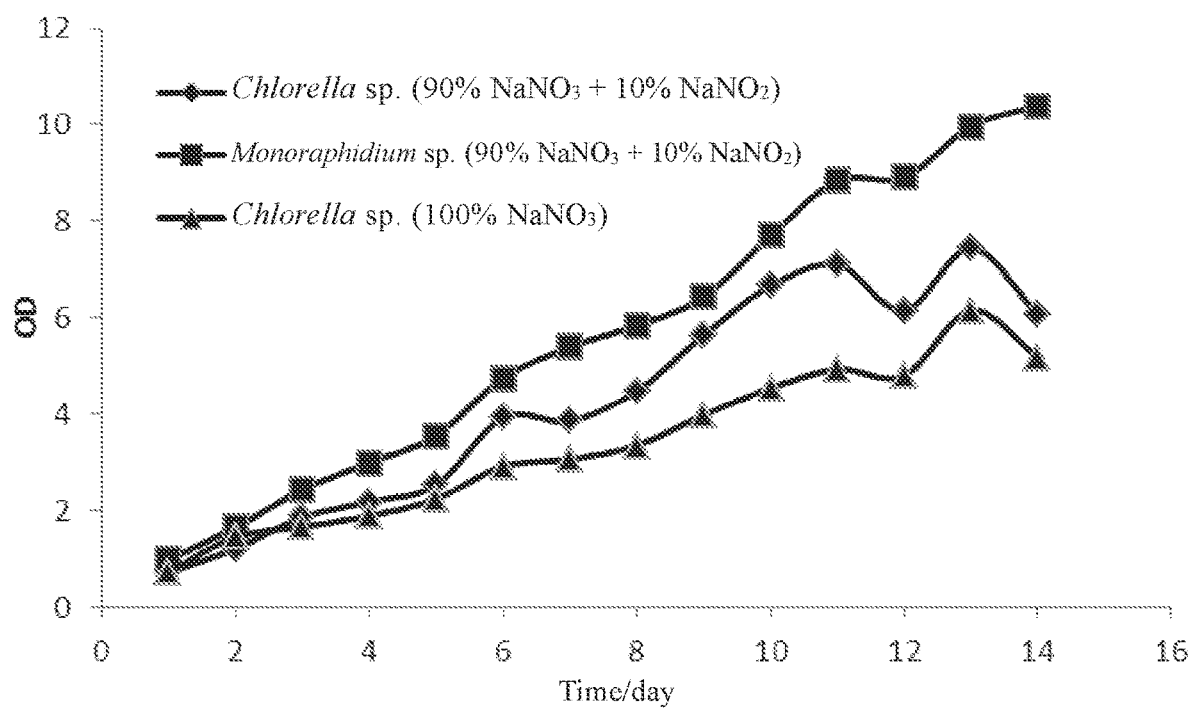
FIG. 3 represents a curve showing the growth of microalgae using a nitrate as the nitrogen source.

It could be seen from FIG. 3 that the microalgae strain selected could grow successfully using either nitrate or nitrite.

Examples 9-16 illustrated the impact of EM bacteria on the metabolism of inorganic nitrogen source by microalgae, with the addition of a great deal of organic carbon source.

Example 9

A BG11 medium (having nutrient ingredients according to Table 1, without sterilization) was firstly used to cultivate *Chlorella* sp. When the $OD_{680}$ value reached 4, an amount of heterotrophic medium nutrient ingredients as specified in Table 4 was supplemented once. The temperature was controlled between 20 and 30° C. Compressed air and $CO_2$ were fed for cultivation. When the microalgae suspension had a pH>10, $CO_2$ was fed, while when the microalgae suspension had a pH<7.5, the feeding of $CO_2$ was ceased. Natural sunlight was used for cultivation. The illumination intensity at daytime was controlled up to 60000 lux. 2 g/L of glucose was added, and EM bacteria was added in an amount of $2.9 \times 10^7$ cells/L microalgae suspension. The $OD_{680}$ value of the microalgae suspension was detected every day. After 1 day of cultivation, 10 g/L of glucose was added again, and EM bacteria was supplemented in an amount of $3.6 \times 10^7$ cells/L microalgae suspension. When the cultivation was conducted to the fifth day, 10 g/L of glucose was supplemented again. During the cultivation, the bacteria count of the microalgae suspension monitored was up to $9.7 \times 10^6$/ml microalgae suspension. Harvest was made after a 8 day continuous cultivation. After the last time of adding glucose, the feeding of $CO_2$ was ceased. At the terminal of the cultivation, the pH of the microalgae suspension was 8.6. A microalgae biomass and a residual cultivation solution were obtained through centrifugal separation. An analysis of the residual cultivation solution showed a total content of $NO_3^-$ and $NO_2^-$ of <10 µg/g. The growth curve of the microalgae was showed in FIG. 4.

Example 10

The example was substantially same as example 9, except that the microalgae cultivated was *Monoraphidium* sp. During the cultivation, the bacteria count of the microalgae suspension monitored was up to $4.6 \times 10^7$/ml microalgae suspension. At the terminal of the cultivation, the pH of the microalgae suspension had increased naturally to 8.2. An analysis of the residual cultivation solution showed a total content of $NO_3^-$ and $NO_2^-$ of <200 µg/g. The growth curve of the microalgae was showed in FIG. 4.

Example 11

The example was substantially same as example 9, except for the following aspects: the amount for the first addition of EM bacteria being $7.9 \times 10^7$ cells/L microalgae suspension, without a second addition of EM bacteria; and the amount for the second addition of glucose being 30 g/L, without a third addition of EM bacteria. During the cultivation, the bacteria count of the microalgae suspension monitored was up to $2.6 \times 10^7$/ml microalgae suspension. At the terminal of the cultivation, the pH of the microalgae suspension had increased naturally to 8.2. An analysis of the residual cultivation solution showed a total content of $NO_3^-$ and $NO_2^-$ of <10 μg/g. The growth curve of the microalgae was showed in FIG. 4.

Example 12

The example was substantially same as example 11, except that the microalgae cultivated was *Monoraphidium* sp. During the cultivation, the bacteria count of the microalgae suspension monitored was up to $5.2 \times 10^7$/ml microalgae suspension. At the terminal of the cultivation, the pH of the microalgae suspension had increased naturally to 7.8. An analysis of the residual cultivation solution showed a total content of $NO_3^-$ and $NO_2^-$ of <200 μg/g. The growth curve of the microalgae was showed in FIG. 4.

Comparative Example 2

The example was substantially same as example 9, except that no EM bacteria was added. During the culture, the bacteria count of the microalgae suspension monitored was up to $13.6 \times 10^8$/ml microalgae suspension. At the cultivation terminal, the pH of the microalgae suspension had increased naturally to 7.2. The growth curve of the microalgae was showed in FIG. 4.

Figure 4:
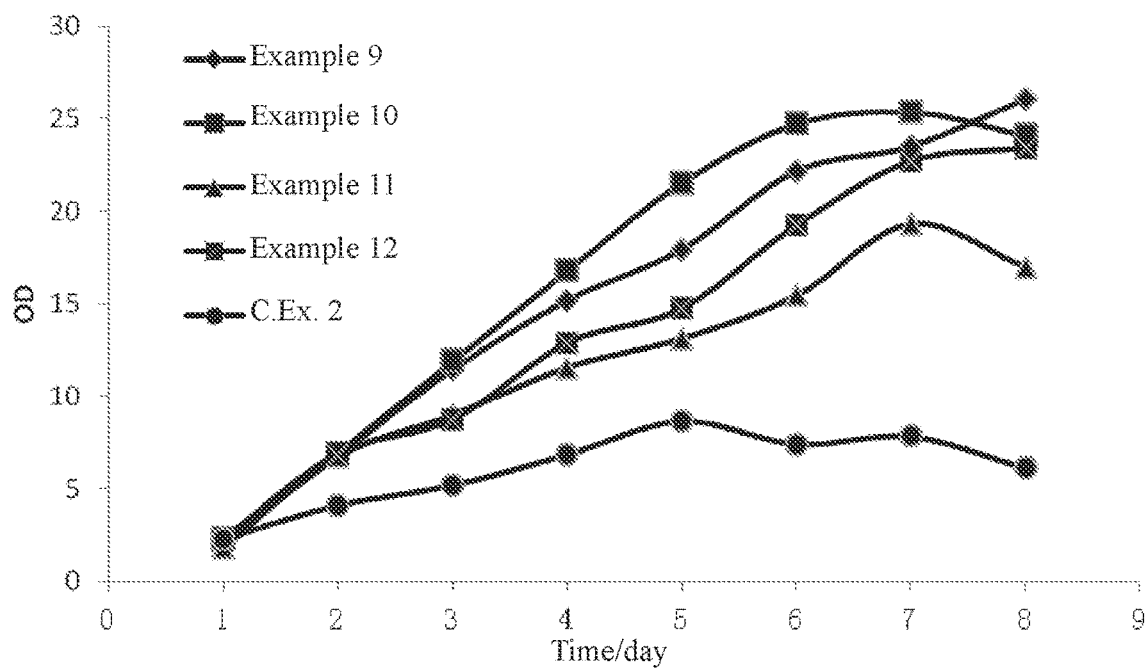
FIGS. 4 and 5 represent curves showing the growth of microalgae with abundant of an organic carbon source.

It could be seen from FIG. 4 that the addition of EM bacteria promoted the growth of microalgae and consumed rapidly the inorganic nitrogen source.

Example 13

A BG11 medium (having nutrient ingredients according to Table 1, without sterilization) was firstly used to cultivate *Chlorella* sp. When the $OD_{680}$ value reached 4, an amount of heterotrophic medium nutrient ingredients as specified in Table 4 was supplemented once. The temperature was controlled between 20 and 30° C. Compressed air and $CO_2$ were fed for cultivation. When the microalgae suspension had a pH>10, $CO_2$ was fed, while when the microalgae suspension had a pH<7.5, the feeding of $CO_2$ was ceased. Natural sunlight was used for cultivation. The illumination intensity at daytime was controlled up to 60000 lux. Since inoculation of *Chlorella* sp., the cultivation was firstly made for 2 days under autotrophic conditions by illumination. Then, 2 g/L of glucose was added. EM bacteria was added in an amount of $1.8 \times 10^8$ cells/L microalgae suspension. The $OD_{680}$ value of the microalgae suspension was detected every day. After 3 day of cultivation, 10 g/L of glucose was added again, and EM bacteria was supplemented in an amount of $1.8 \times 10^8$ cells/L microalgae suspension. After 2 days of cultivation, 10 g/L of glucose was supplemented again. During the cultivation, the bacteria count of the microalgae suspension monitored was up to $2.9 \times 10^7$ cells/ml microalgae suspension. Harvest was made after a 14 day continuous cultivation. After the last time of adding glucose, the feeding of $CO_2$ was ceased. At the terminal of the cultivation, the pH of the microalgae suspension was 9.2. A microalgae biomass and a residual cultivation solution were obtained through centrifugal separation. An analysis of the residual cultivation solution showed a total content of $NO_3^-$ and $NO_2^-$ of <10 μg/g. The growth curve of the microalgae was showed in FIG. 5.

Example 14

The example was substantially same as example 13, except for the following aspects: the absence of a second addition of EM bacteria; and the amount for the second addition of glucose being 30 g/L, without a third addition of EM bacteria. During the cultivation, the bacteria count of the microalgae suspension monitored was up to $2.9 \times 10^7$/ml microalgae suspension. At the terminal of the cultivation, the pH of the microalgae suspension had increased naturally to 9.3. An analysis of the residual cultivation solution showed a total content of $NO_3^-$ and $NO_2^-$ of <10 μg/g. The growth curve of the microalgae was showed in FIG. 5.

Example 15

The example was substantially same as example 13, except that $NaNO_3$ in the BG11 medium was replaced with $KNO_3$, and $KNO_3$ was added in an amount of 0.5 g/L. During the cultivation, the bacteria count of the microalgae suspension monitored was up to $1.3 \times 10^7$/ml microalgae suspension. At the terminal of the cultivation, the pH of the microalgae suspension was 9.4. An analysis of the residual cultivation solution showed a total content of $NO_3^-$ and $NO_2^-$ of <10 μg/g. The growth curve of the microalgae was showed in FIG. 5.

Example 16

The example was substantially same as example 14, except that $NaNO_3$ in the BG11 medium was replaced with $KNO_3$, and $KNO_3$ was added in an amount of 0.5 g/L. During the cultivation, the bacteria count of the microalgae suspension monitored was up to $1.7 \times 10^7$/ml microalgae suspension. At the terminal of the cultivation, the pH of the microalgae suspension was 9.3. An analysis of the residual cultivation solution showed a total content of $NO_3^-$ and $NO_2^-$ of <10 μg/g. The growth curve of the microalgae was showed in FIG. 5.

Figure 5:
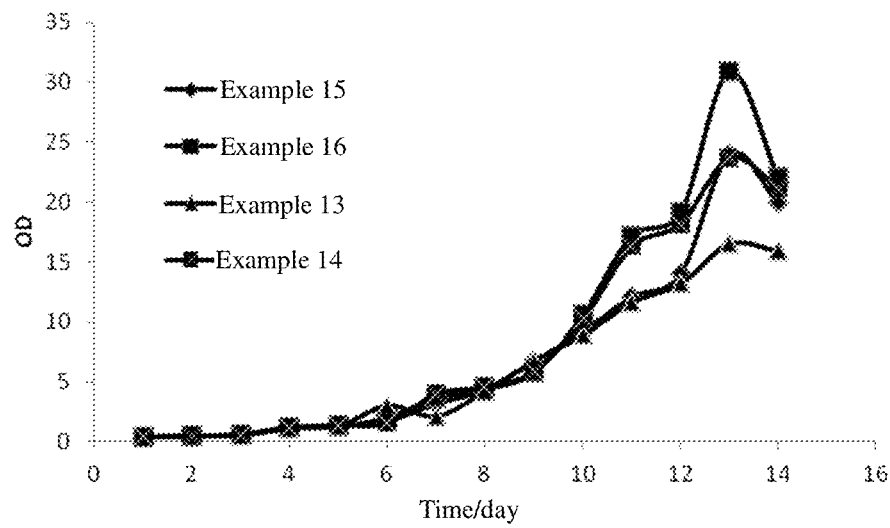

It could be seen from FIG. 5 that using either potassium nitrate or sodium nitrate as the nitrogen source, the addition of EM bacteria promoted the growth of microalgae.

Examples 17-18 illustrated the immobilization of NOx using a residual cultivation solution obtained from a microalgae cultivation and a continued microalgae cultivation using the NOx immobilized solution.

Example 17

NOx was absorbed by the assistance of $O_3$.

A mixed gas of $NO_2$ and NO was used to simulate a practical flue gas. A compressed air was used as carrier gas. The flow rate of NOx was 0.3 L/min. A $O_3$-containing gas was provided by a Model XM-Y movable ozonizer available from Qingdao Xin Mei purification equipment Co., Ltd., with a flow rate of 1 L/min. Air was mixed to a total flow rate of 150 L/h. NOx concentrations in the inlet and outlet gas outlet gases were measured. A NOx immobilizing ratio was calculated as:

NOx immobilizing ratio=(1−NOx concentration at the outlet/NOx concentration at the inlet)× 100%;

wherein the total concentration of NOx at the inlet was substantially stable at 620 mg/m³ (with a NO content of about 600 mg/m³ and a $NO_2$ content of about 20 mg/m³)

Figure 6:
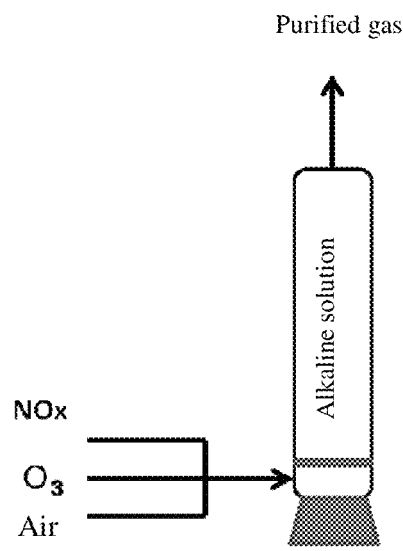
FIG. 6 represents a flow chart showing a NOx immobilizing process.

The flow chart was showed in FIG. 6. The absorption column had a diameter of 100 mm and a height of 700 mm.

The column bottom was equipped with a sieve gas distributor. 3 L of the residual cultivation solution generated from example 16 was contained in the column. During operation, a NOx mixed gas was fed directly into the absorption column. The operation was ceased after 22 h. The residual cultivation solution within the column was taken out, and was measured for the total content of $NO_3^-$ and $NO_2^-$ of 5900 μg/g.

Microalgae was cultivated using the NOx immobilized solution.

Figure 7:
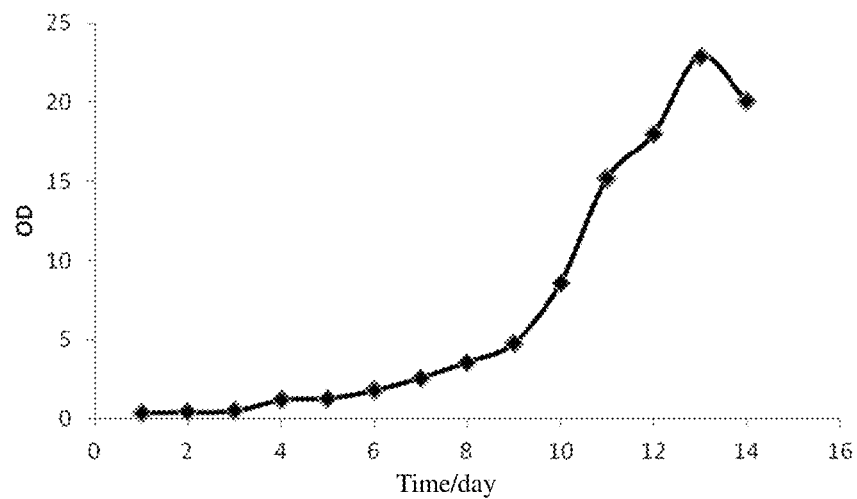
FIGS. 7 and 8 represent curves showing the growth of microalgae using a NOx immobilized nutrient stream as the nitrogen source.

The NOx immobilized solution above was used as microalgae medium to cultivate *Chlorella* sp., where the other nutrient substances than the nitrogen source were provided referring to BG11 medium. The other portions of the cultivation process were same as example 16. During the cultivation, the bacteria count of the microalgae suspension monitored was up to $1.8 \times 10^7$/ml microalgae suspension. Harvest was made after a 14 day continuous cultivation. After the last time of adding glucose, the feeding of $CO_2$ was ceased. At the terminal of the cultivation, the pH of the microalgae suspension was 9.1. A microalgae biomass and a residual cultivation solution were obtained through centrifugal separation. An analysis of the residual cultivation solution showed a total content of $NO_3^-$ and $NO_2$ of <10 μg/g. It could be seen from FIG. 7 that using the NOx immobilized nutrient stream as a cultivation nutrient solution, the growth of microalgae was promoted after the addition of EM bacteria, by which $NO_3^-$ and $NO_2^-$ in the microalgae suspension was immobilized again and the microalgae suspension was reverted back to be alkaline, so as to be further used as an alkaline immobilizing solution for the waste gas denitration.

Example 18

The example was substantially same as example 17, except that 3 L of residual cultivation solution obtained from example 10 was contained in the absorption column. After 22 h of immobilization, the residual cultivation solution in the column was taken out, which was measured to have a total content of $NO_3^-$ and $NO_2^-$ of 5800 μg/g.

Microalgae was cultivated using the NOx immobilized solution.

Figure 8:
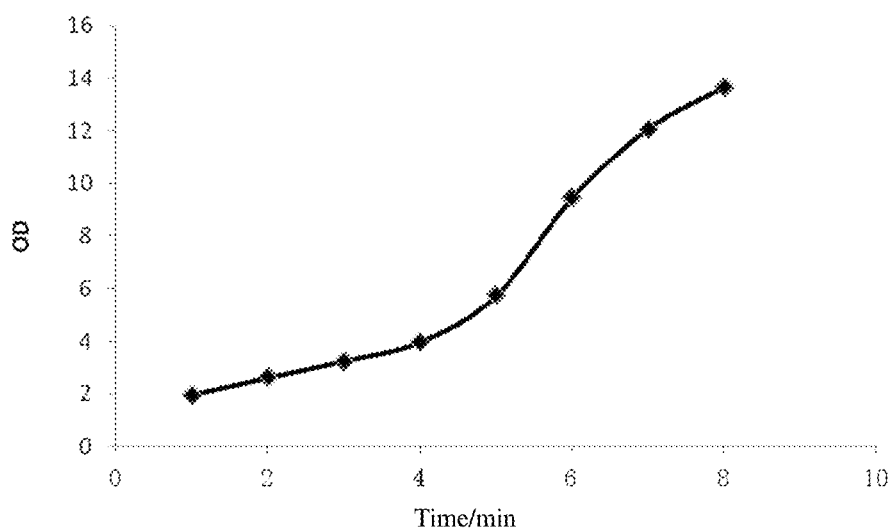

The NOx immobilized solution above was used as microalgae medium to cultivate *Monoraphidium* sp., where the other nutrient substances than the nitrogen source were provided referring to BG11 medium. The other portions of the cultivation process were same as example 10. During the cultivation, the bacteria count of the microalgae suspension monitored was up to $9.2 \times 10^6$/ml microalgae suspension. Harvest was made after a 8 day continuous cultivation. After the last time of adding glucose, the feeding of $CO_2$-containing flue gas was ceased. At the terminal of the cultivation, the pH of the microalgae suspension was 8.7. A microalgae biomass and a residual cultivation solution were obtained through centrifugal separation. An analysis of the residual cultivation solution showed a total content of $NO_3^-$ and $NO_2^-$ of <200 μg/g. It could be seen from FIG. 8 that using the NOx immobilized solution as a cultivation nutrient solution, the growth of microalgae was promoted after the addition of EM bacteria, by which $NO_3^-$ and $NO_2^-$ in the microalgae suspension was immobilized again and the microalgae suspension was reverted back to be alkaline, so as to be further used as an alkaline immobilizing solution for the waste gas denitration.

The example illustrated the impact of EM bacteria on the growth of microalgae under heterotrophic conditions without light.

Example 19

Figure 9:
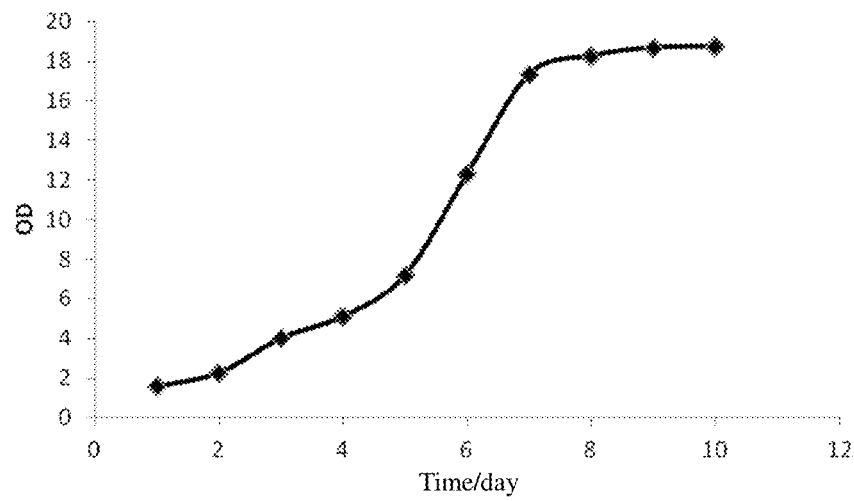
FIG. 9 represents a curve showing the growth of microalgae added with EM bacteria under heterotrophic conditions without light.

The example was substantially same as example 9, except that the microalgae cultivated under conditions without light. The pH of the microalgae suspension at the terminal of cultivation was measured as 7.7. The growth curve of the microalgae was showed in FIG. 9.

Comparative Example 3

The comparative example illustrated the nitrate assimilation by EM bacteria.

The present comparative example was substantially same as example 9, except that: only the cultivation of EM bacteria was conducted; the medium was sterilized before cultivation; the medium was still BG11 (Table 1), whilst the initial concentration of $NO_3^-$ was 6900 ug/g; and the cultivation lasted for 14 days. An analysis at the cultivation terminal showed a total content of $NO_3^-$ and $NO_2^-$ of 5600 μg/g. It could be seen that, during the growth, EM bacteria consumed the inorganic nitrogen source with a much less rate than that of microalgae.

Example 20

The example illustrated the immobilization of NOx using an alkaline residual cultivation solution.

3 L of the alkaline residual cultivation solution from example 14 was analyzed for the concentrations of potassium and sodium ions. 3 L of an aqueous solution having same potassium ion concentration and sodium ion concentration was formulated, where the pairing anions were $HCO_3^-$ and $CO_3^{2-}$. The aqueous solution formulated had a pH of 9.27, substantially same as that of the alkaline residual cultivation solution from example 14. The aforementioned alkaline residual cultivation solution and the formulated aqueous solution were used respectively as a immobilizing solution to immobilize NOx using the process of example 17. A curve showing the efficiency of immobilizing NOx was provided in FIG. 10.

Figure 10:
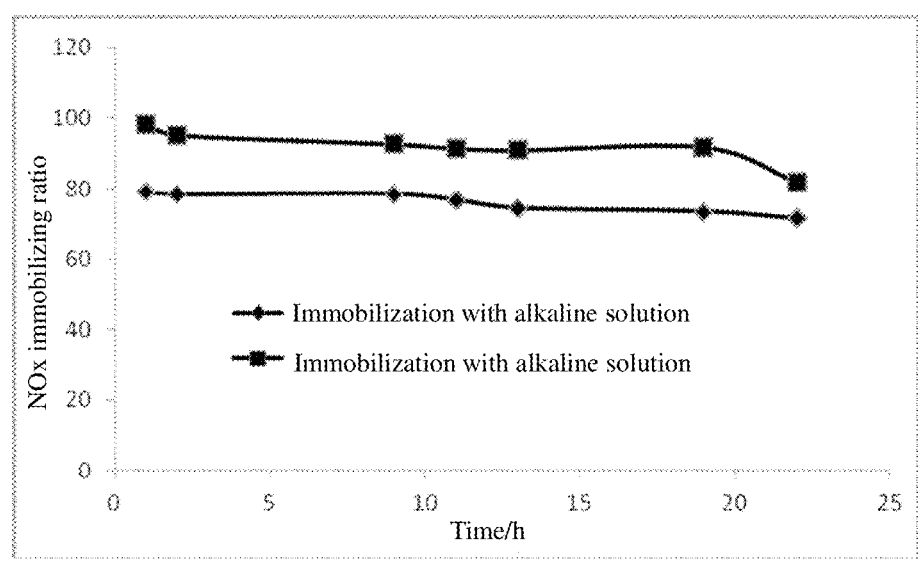
FIG. 10 represents a curve showing the NOx immobilizing rate over time.

It could be seen from FIG. 10 that the residual cultivation solution had a significantly higher efficiency of immobilizing NOx than that of the formulated alkaline solution.

Comparative Example 4

The comparative example illustrated the effect of cultivating *Chlorella* sp. with low concentration of $NH_4HCO_3$.

BG11 medium (Table 1) was used to cultivate *Chlorella* sp., while the nitrogen source in the BG11 medium was replaced with $NH_4HCO_3$ having a concentration of 3.3 mmol/L, which was much less than that of the BG11 medium (17.6 mmol/L). The initial concentration of the microalgae strain, $OD_{680}$, was 0.5. Compressed air was fed for cultivation. The temperature was controlled between 20-30° C. During the culture, natural sunlight was used for cultivation, and the illumination intensity on daytime was controlled up to 60000 lux. The growth curve was provided in FIG. 11.

Comparative Example 5

The comparative example illustrated the effect of cultivating *Chlorella* sp. with low concentration of $NaNO_3$.

The comparative example was substantially same as comparative example 4, except that the nitrogen source in the medium was replaced with $NaNO_3$. The $OD_{680}$ value of the microalgae suspension was detected every day. The growth curve was provided in FIG. 11.

Comparative Example 6

The comparative example illustrated the effect of cultivating *Chlorella* sp. with extra high concentration of $NaNO_3$.

The comparative example was substantially same as comparative example 4, except that the nitrogen source in the medium was replaced with $NaNO_3$, while the concentration of the nitrogen source was increased to 176 mmol/L, which was much higher than that of the BG11 medium (17.6 mmol/L). The $OD_{680}$ value of the microalgae suspension was detected every day. The growth curve was provided in FIG. 11.

Example 20

The example illustrated the effect of an autotrophic culture of *Chlorella* sp. according to the present invention.

The example was substantially same as comparative example 4, except that the nitrogen source and the concentration thereof still followed the formulation of BG11 medium, and when the pH was higher than 10 during the late stage of the cultivation, nitric acid was supplemented to adjust the pH in an appropriate range. The $OD_{680}$ value of the microalgae suspension was detected every day. The growth curve was provided in FIG. 11.

Example 21

The example illustrated the effect of an autotrophic culture of *Spirulina* sp. according to the present invention.

Z-medium (Table 3) was used to cultivate *Spirulina* sp. The microalgae strain had an initial concentration, $OD_{680}$, of 0.3. Compressed air was fed for cultivation. The temperature was controlled between 20-30° C. When the pH was higher than 10.5 during the late stage of the cultivation, nitric acid was supplemented to adjust the pH in an appropriate range. During the culture, natural sunlight was used for cultivation, and the illumination intensity on daytime was controlled up to 60000 lux. The $OD_{680}$ value of the microalgae suspension was detected every day. The growth curve was provided in FIG. 12.

Example 22

The example illustrated the effect of a mixotrophic cultivation of *Chlorella* sp. according to the present invention (without sterilization).

The example was substantially same as comparative example 4, except that a heterotrophic cultivation medium for *Chlorella* sp. (Table 4) was used. 2 g/L of glucose and EM bacteria in an amount of 5×10⁷ cells/L microalgae suspension were added every three days during the culture, and when the pH was higher than 10, nitric acid was supplemented to adjust the pH in an appropriate range. The $OD_{680}$ value of the microalgae suspension was detected every day. The growth curve was provided in FIG. 11.

Example 23

The example illustrated the effect of a mixotrophic cultivation of *Spirulina* sp. according to the present invention (without sterilization).

The example was substantially same as example 21, except that 2 g/L of glucose and EM bacteria in an amount of 5×10.5⁷ cells/L microalgae suspension were added every three days during the culture, and when the pH was higher than 10.5, nitric acid was supplemented to adjust the pH in an appropriate range. The $OD_{680}$ value of the microalgae suspension was detected every day. The growth curve was provided in FIG. 12.

Example 24

The example illustrated the effect of an aseptic heterotrophic cultivation of *Chlorella* sp. according to the present invention.

The example was substantially same as comparative example 4, using a *Chlorella* sp. heterotrophic medium (Table 4) for heterotrophic cultivation. The microalgae strain had an initial concentration, $OD_{680}$, of 0.5. Compressed air was fed. The culture was conducted under an aseptic state without light. The temperature was controlled between 20-30° C. When the glucose was consumed substantially, 10 g/L of glucose was added in time; while when the pH was higher than 10, nitric acid was supplemented to adjust the pH in an appropriate range. The $OD_{680}$ value of the microalgae suspension was detected every day. The growth curve was provided in FIG. 11.

Figure 11:
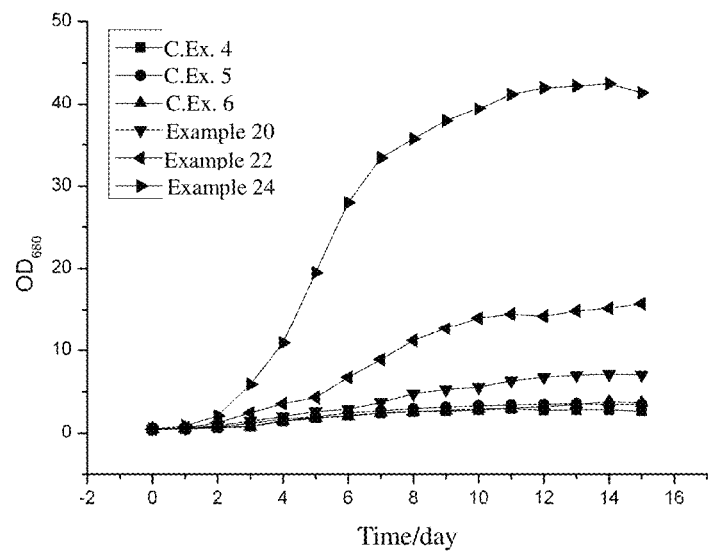
FIG. 11 represents a curve showing the growth of *Chlorella* sp. under different conditions.
Figure 12:
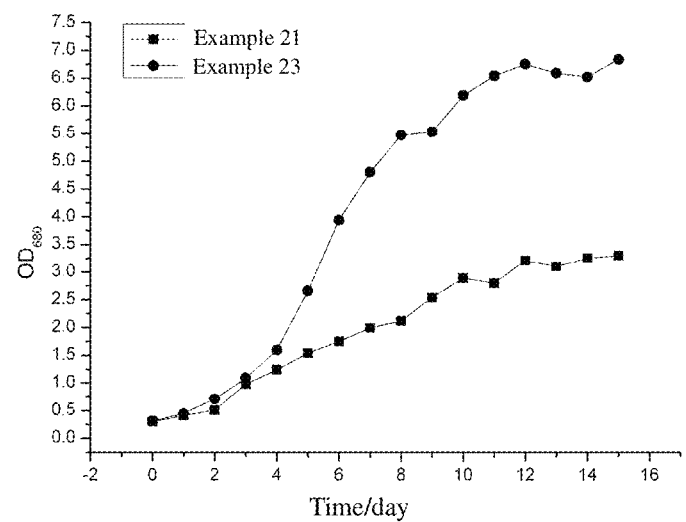
FIG. 12 represents a curve showing the growth of *Spirulina* sp. under different conditions.

It could be seen from FIGS. 11-12 that the process according to the present invention increased the growth efficiency of microalgae. If abundant of nitrate was added at the initial stage of cultivation, the high concentration of nitrate would not promote significantly the growth of microalgae.

Example 25

The example illustrated the impact of the varied concentration of nitric acid or $H_2O_2$ on the hydrogen peroxide decomposition.

Nitric acid/$H_2O_2$ aqueous solutions with various concentrations were formulated. After 10 days, the concentration of $H_2O_2$ was determined. The decomposition rate of $H_2O_2$ in the different concentrations of nitric acid/$H_2O_2$ aqueous solutions were accordingly calculated, results provided in Table 6. (the concentration of hydrogen peroxide was measured referring to the process of GB1616-2003)

TABLE 6

| | Hydrogen peroxide | | |
|---|---|---|---|
| Nitric acid | 6 wt % | 3 wt % | 0.3 wt % |
| 35 wt % | 25% | 23% | 19.3% |
| 25 wt % | 16% | 15.5% | 12% |
| 15 wt % | 9% | 7.3% | 5.4% |

It could be seen from Table 6 that despite increasing the concentration of nitric acid or increasing the concentration of hydrogen peroxide, the dissipation of hydrogen peroxide was increased significantly.

Example 26

The example illustrated the effect of the denitration of a low concentration of NOx according to the present invention.

A simulate waste gas was formulated by NO, $NO_2$ and nitrogen gas, with a NO concentration of 500 ppm (volume) and a $NO_2$ concentration of 20 ppm (volume). The absorption solution consisted of 15 m % of nitric acid, 0.4 m % of hydrogen peroxide and balance of water. The absorption device was a glass column, having a diameter of 100 mm and a height of 700 mm. The glass column was equipped at the bottom with a sieve plate, having a hole diameter of 16 μm-30 μm. The column contained 3000 ml of absorption solution. The flow rate of the simulate waste gas was 150 L/h. The test was carried out at room temperature under atmospheric pressure. The test result was provided in Table 7. (referring to the process of GB/T14642-2009, no nitrite was found in the absorption solution after the test)

TABLE 7

| Treatment time/h | 1 | 2 | 4 | 8 | 12 | 16 | 20 | 26 | 31 | 36 | 41 | 47 |
|---|---|---|---|---|---|---|---|---|---|---|---|---|
| Outlet NO/ppm | 460 | 420 | 360 | 260 | 150 | 35 | 30 | 24 | 20 | 17 | 21 | 19 |
| Outlet $NO_2$/ppm | 1 | 0 | 0 | 0 | 0 | 5 | 10 | 13 | 18 | 23 | 19 | 21 |
| Outlet NOx/ppm | 461 | 420 | 360 | 260 | 150 | 40 | 40 | 37 | 38 | 40 | 40 | 40 |

It could be seen from Table 7 that at the initial stage of denitration, the denitration activity of the absorption solution was very low. The denitration activity of the absorption solution increased gradually and successively over time. 16 hours later, the denitration activity of the absorption solution reached a stable stage, where the denitration ratio was more than 90%.

Example 27

The example illustrated the effect of the denitration of a low concentration of NOx according to the present invention.

The example was substantially same as example 26, except that the concentration of hydrogen peroxide was 1 m %, and the concentration of nitric acid was 25 m %. The test result was provided in Table 8. (referring to the process of GB/T14642-2009, no nitrite was found in the absorption solution after the test)

TABLE 8

| Time/h | 1 | 2 | 4 | 8 | 12 | 16 | 20 |
|---|---|---|---|---|---|---|---|
| Outlet $NO_2$/ppm | 0 | 0 | 0 | 0 | 0 | 2 | 11 |
| Outlet NOx/ppm | 430 | 400 | 330 | 220 | 100 | 38 | 38 |

Example 28

The example illustrated the effect of the denitration of a high concentration of NOx using a single column according to the present invention.

The example was substantially same as example 26, except that the concentration of hydrogen peroxide was 0.3 m %, and the concentration of nitric acid was 15 m %; and the simulate waste gas had a NO concentration of 3200 ppm (volume) and a $NO_2$ concentration of 100 ppm (volume). The test result was provided in Table 9. (referring to the process of GB/T14642-2009, no nitrite was found in the absorption solution after the test)

TABLE 9

| Time/h | 1 | 2 | 4 | 8 | 12 | 16 | 20 | 24 | 30 | 35 | 40 | 45 |
|---|---|---|---|---|---|---|---|---|---|---|---|---|
| Outlet NO/ppm | 2310 | 1900 | 1600 | 1400 | 1300 | 1250 | 1200 | 1000 | 830 | 750 | 800 | 830 |
| Outlet $NO_2$/ppm | 60 | 50 | 35 | 35 | 30 | 30 | 50 | 120 | 290 | 320 | 290 | 260 |
| Outlet NOx/ppm | 2370 | 1950 | 1635 | 1435 | 1330 | 1280 | 1250 | 1120 | 1110 | 1070 | 1090 | 1090 |

Comparative Example 7

The comparative example illustrated the effect of denitration using a high concentration of $H_2O_2$.

The example was substantially same as example 26, except that the concentration of hydrogen peroxide was 2.5 m %, and the concentration of nitric acid was 15 m %. The test result was provided in Table 10.

TABLE 10

| Time/h | 1 | 2 | 4 | 8 | 12 | 16 | 20 |
|---|---|---|---|---|---|---|---|
| NO/ppm | 59 | 20 | 50 | 30 | 25 | 25 | 35 |
| $NO_2$/ppm | 14 | 25 | 15 | 20 | 20 | 15 | 10 |
| NOx/ppm | 73 | 45 | 75 | 50 | 45 | 40 | 35 |

Example 29

The example illustrated a process involving the acid procedure using the system according to the present invention.

Referring to FIG. 14, 150 L/h of a mixed gas comprising 480 ppm of NO and balance of air was firstly fed into denitration reactor 1-1 (containing 0.5% aqueous hydrogen peroxide and 15% aqueous dilute nitric acid solution) for reaction to provide a dilute nitric acid. The yield of nitric acid was 0.19 kg/h. The purified gas C after immobilization was vented.

3 kg of microalgae nutrient solution E was fed into NOx immobilizing nutrient stream formulating device 1-2 (the nutrient solution consisting of Z-medium +10 g/L $NaNO_3$), mixed homogeneously with residual cultivation solution F and dilute nitric acid, and fed into microalgae cultivation device 2, to which a concentration of microalgae strain D was added to provide a final microalgae suspension concentration of OD=0.3. $CO_2$ with a concentration of 2% (by volume) was fed into the microalgae cultivating device 2 at a flow rate of 200 L/h.

When the pH of the microalgae suspension <8.5, the feeding of $CO_2$ was ceased; while when the pH of the microalgae suspension >10.5, the feeding of $CO_2$ was continued. The illumination intensity was 10000 lux.

After the completion of cultivation, the microalgae suspension was fed into microalgae filter separator 3 for filtration and separation, and 2.5 kg of residual cultivation solution F obtained therefrom was returned to NOx immobilizing nutrient stream formulating device 1-2 for recycle cultivation. 250 g of concentrated microalgae biomass G was fed into microalgae dryer 4 for drying, to provide 25 g of microalgae product.

The invention claimed is:

1. A process of cultivating microalgae, comprising:
washing an industrial waste gas using an absorption solution comprising 0.5 mass % to 58 mass % of nitric acid and 0.001 mass % to 25 mass % of hydrogen peroxide to obtain a purified gas and a NOx immobilized solution;
forming a NOx immobilized nutrient stream comprising the NOx immobilized solution and a residual cultivation solution;
preparing a microalgae suspension;
adding the NOx immobilized nutrient stream to the microalgae suspension;
adding effective microorganisms (EM) to the microalgae suspension, wherein the EM comprises photosynthetic bacteria, lactobacillus, yeast, gram-positive actinomyces, and filamentous bacteria;
growing microalgae in the microalgae suspension; and
separating the microalgae suspension into a microalgae biomass and the residual cultivation solution,
wherein the industrial waste gas comprises NOx, and
wherein the NOx immobilized nutrient stream comprises a nitrogen source that is $NO^{3-}$, $NO^{2-}$, or a mixture thereof and an amount of nitrogen source, calculated as nitrogen atoms, is 10-300 mmol/L.

2. The process according to claim 1, wherein the microalgae is a heterotrophic or mixotrophic microalgae.

3. The process according to claim 2, wherein the microalgae is selected from the group consisting of Cyanophyta and Chlorophyta.

4. The process according to claim 2, wherein the microalgae is *Chlorella* sp., *Scenedesmus* sp., *Monoraphidium* sp. or *Spirulina* sp.

5. The process according to claim 1, further comprising adding into the NOx immobilized nutrient stream an organic carbon source selected from the group consisting of sugar, organic acid, salt of an organic acid, alcohol, cellulose hydrolyzate, starch hydrolyzate, and mixtures thereof.

6. The process according to claim 5, wherein a concentration of the organic carbon source is 1 g/L microalgae suspension to 30 g/L microalgae suspension.

7. The process according to claim 1, wherein the EM bacteria is added in an amount of $1\times10^5$ cells/L microalgae suspension to $9\times10^8$ cells/L microalgae suspension.

8. The process according to claim 1, wherein the microalgae suspension has a temperature of 15° C. to 40° C. and a pH of 6-11.

9. The process according to claim 1, further comprising illuminating the microalgae suspension at an illumination intensity of 1000-200000 lux.

10. The process according to claim 1, wherein the nutrient stream comprises at least a nitrogen source, a phosphorus source, and a carbon source, wherein at least one of the nitrogen source, the phosphorus source, and the carbon source is in the form of an alkali nutrient salt, wherein, during the cultivation, the pH of the microalgae suspension is adjusted using nitric acid, nitrous acid, or a mixture thereof.

11. The process according to claim 5, wherein the organic carbon source is selected from the group consisting of glucose, levulose, acetic acid, sodium acetate, lactic acid, ethanol, methanol, cellulose hydrolyzate, and mixtures thereof.

12. The process according to claim 1, further comprising: separating the microalgae suspension to obtain a residual cultivation solution and microalgae; and washing an industrial waste gas using the residual cultivation solution to obtain the NOx immobilized nutrient stream, wherein the industrial waste gas contains NOx.

13. The process according to claim 1, wherein the amount of the nitrogen-containing compound in the NOx immobilized nutrient stream is 20-200 mmol/L.

* * * * *